US012533251B2

(12) United States Patent
Gunnsteinsson et al.

(10) Patent No.: US 12,533,251 B2
(45) Date of Patent: Jan. 27, 2026

(54) ORTHOPEDIC WALKER

(71) Applicant: Ossur Iceland ehf, Reykjavik (IS)

(72) Inventors: Larus Gunnsteinsson, Reykjavik (IS); Sindri Pall Sigurdsson, Reykjavik (IS); Jane Price, Foothill Ranch, CA (US); Asdis Bjornsson, Reykjavik (IS); Matthew Barrientos, Foothill Ranch, CA (US)

(73) Assignee: OSSUR ICELAND EHF, Reykjavik (IS)

(*) Notice: Subject to any disclaimer, the term of this patent is extended or adjusted under 35 U.S.C. 154(b) by 0 days.

(21) Appl. No.: 17/528,971

(22) Filed: Nov. 17, 2021

(65) Prior Publication Data

US 2022/0151812 A1 May 19, 2022

Related U.S. Application Data

(60) Provisional application No. 63/213,391, filed on Jun. 22, 2021, provisional application No. 63/115,804, filed on Nov. 19, 2020.

(51) Int. Cl.
*A61F 5/11* (2006.01)
*A61F 5/01* (2006.01)

(52) U.S. Cl.
CPC ............ *A61F 5/0111* (2013.01); *A61F 5/012* (2013.01); *A61F 5/0195* (2013.01)

(58) Field of Classification Search
CPC .......... A61F 5/01; A61F 5/012; A61F 5/0111; A61F 5/0195; A61F 5/0102;
(Continued)

(56) References Cited

U.S. PATENT DOCUMENTS

| | | |
|---|---|---|
| 346,606 A | 8/1886 | Pugsley |
| 975,576 A | 11/1910 | Sexton |

(Continued)

FOREIGN PATENT DOCUMENTS

| | | |
|---|---|---|
| CN | 101711141 A | 5/2010 |
| CN | 102026592 A | 4/2011 |

(Continued)

OTHER PUBLICATIONS

International Search Report from PCT Application No. PCT/US2019/016462, May 17, 2019.

(Continued)

*Primary Examiner* — Adam Baker
(74) *Attorney, Agent, or Firm* — Workman Nydegger

(57) ABSTRACT

An orthopedic walker includes a body formed from at least one polymeric material and having a unitary construction. The body forms first and second portions divided by a median plane and connected to one another by a footbed. The first and second portions extend from the footbed and form an interior volume for receiving a foot and lower leg of a user. The first and second portions are arranged to articulate about or from the median plane to expand and retract the interior volume. The body consists of the first and second portions, and the footbed inclusive of an outsole having a tread as a continuous structure formed unitarily from the at least one polymeric material. The at least one polymeric material is an expanded thermoplastic.

18 Claims, 18 Drawing Sheets

(58) Field of Classification Search
CPC .......... A61F 2250/0003; A61F 5/05816; A61F 5/0113; A61F 5/0127; A61F 5/0585; A43B 17/023; A43B 17/018; A43B 7/144; A43B 13/12; A43B 13/122; A43B 13/22; A43B 13/223; A43B 1/10
USPC .......................................................... 602/27
See application file for complete search history.

(56) References Cited

U.S. PATENT DOCUMENTS

| | | | | |
|---|---|---|---|---|
| 1,012,017 | A | | 12/1911 | Salt |
| 2,200,849 | A | | 5/1940 | Margolin |
| 2,236,367 | A | | 3/1941 | Gruber |
| 2,292,297 | A | | 8/1942 | Sherlock |
| 2,444,640 | A | | 7/1948 | Epstein |
| 2,868,191 | A | | 1/1959 | Juhasz |
| 2,885,797 | A | | 5/1959 | Chrencik |
| 2,888,016 | A | | 5/1959 | De Lamater |
| 2,909,854 | A | | 10/1959 | Edelstein |
| 2,913,837 | A | | 11/1959 | Geuder |
| 2,917,844 | A | | 12/1959 | Scholl |
| 2,928,193 | A | | 3/1960 | Kristan |
| 2,979,835 | A | | 4/1961 | Scholl |
| 2,979,836 | A | | 4/1961 | Scholl |
| 3,270,358 | A | | 9/1966 | Milner |
| 3,464,126 | A | | 9/1969 | Sarkissian |
| 3,548,420 | A | | 12/1970 | Spence |
| 3,580,248 | A | | 5/1971 | Larson |
| 3,681,860 | A | | 8/1972 | Bidegain |
| 3,685,176 | A | | 8/1972 | Rudy |
| 3,730,169 | A | | 5/1973 | Fiber |
| 3,735,758 | A | | 5/1973 | Novotney |
| 3,760,056 | A | | 9/1973 | Rudy |
| 3,786,805 | A | | 1/1974 | Tourin |
| 3,792,537 | A | | 2/1974 | Plank et al. |
| 3,814,088 | A | | 6/1974 | Raymond |
| 3,834,377 | A | | 9/1974 | Lebold |
| 3,859,740 | A | | 1/1975 | Kemp |
| 3,922,800 | A | | 12/1975 | Miller et al. |
| 3,955,565 | A | | 5/1976 | Johnson, Jr. |
| 4,045,888 | A | | 9/1977 | Oxenberg |
| 4,057,056 | A | | 11/1977 | Payton |
| 4,095,353 | A | | 6/1978 | Foldes |
| 4,100,686 | A | | 7/1978 | Sgarlato et al. |
| 4,142,307 | A | | 3/1979 | Martin |
| 4,177,583 | A | | 12/1979 | Chapman |
| 4,184,273 | A | | 1/1980 | Boyer et al. |
| 4,217,706 | A | | 8/1980 | Vartanian |
| 4,217,893 | A | | 8/1980 | Payton |
| 4,232,459 | A | | 11/1980 | Vaccari |
| 4,237,626 | A | | 12/1980 | Brown |
| 4,267,649 | A | | 5/1981 | Smith |
| 4,300,294 | A | | 11/1981 | Riecken |
| 4,333,248 | A | | 6/1982 | Samuels |
| 4,370,818 | A | | 2/1983 | Simoglou |
| 4,408,402 | A | | 10/1983 | Looney |
| 4,414,965 | A | | 11/1983 | Mauldin et al. |
| D272,281 | S | | 1/1984 | Alush |
| 4,446,856 | A | * | 5/1984 | Jordan .................. A61F 5/0111 602/27 |
| 4,494,536 | A | | 1/1985 | Latenser |
| 4,505,269 | A | | 3/1985 | Davies et al. |
| 4,550,721 | A | | 11/1985 | Michel |
| 4,565,017 | A | | 1/1986 | Ottieri |
| 4,571,853 | A | | 2/1986 | Medrano |
| 4,572,169 | A | | 2/1986 | Mauldin et al. |
| 4,587,962 | A | | 5/1986 | Greene et al. |
| 4,598,484 | A | | 7/1986 | Ma |
| 4,599,811 | A | | 7/1986 | Rousseau |
| 4,608,768 | A | | 9/1986 | Cavanagh |
| 4,620,378 | A | | 11/1986 | Sartor |
| 4,633,598 | A | | 1/1987 | Moronaga et al. |
| 4,633,599 | A | | 1/1987 | Morell et al. |
| 4,633,877 | A | | 1/1987 | Pendergast |
| 4,638,794 | A | | 1/1987 | Grisar |
| 4,660,300 | A | | 4/1987 | Morell et al. |
| 4,669,202 | A | | 6/1987 | Ottieri |
| 4,674,204 | A | | 6/1987 | Sullivan et al. |
| 4,674,205 | A | | 6/1987 | Anger |
| 4,677,767 | A | | 7/1987 | Darby |
| 4,680,878 | A | | 7/1987 | Pozzobon et al. |
| 4,689,898 | A | | 9/1987 | Fahey |
| 4,719,710 | A | | 1/1988 | Pozzobon |
| 4,727,661 | A | | 3/1988 | Kuhn |
| 4,741,115 | A | | 5/1988 | Pozzobon |
| 4,748,726 | A | | 6/1988 | Schoch |
| 4,760,653 | A | | 8/1988 | Baggio |
| 4,771,768 | A | | 9/1988 | Crispin |
| 4,773,170 | A | | 9/1988 | Moore et al. |
| 4,793,078 | A | | 12/1988 | Andrews |
| D299,787 | S | | 2/1989 | Bates |
| 4,805,321 | A | | 2/1989 | Tonkel |
| 4,805,601 | A | | 2/1989 | Eischen, Sr. |
| 4,811,504 | A | * | 3/1989 | Bunke .................. A43B 5/0419 36/25 R |
| 4,869,001 | A | | 9/1989 | Brown |
| 4,872,273 | A | | 10/1989 | Smeed |
| 4,879,822 | A | | 11/1989 | Hayes |
| 4,893,418 | A | | 1/1990 | Ogden |
| 4,934,355 | A | | 6/1990 | Porcelli |
| 4,947,838 | A | | 8/1990 | Giannetti |
| 4,974,583 | A | | 12/1990 | Freitas |
| 5,056,509 | A | | 10/1991 | Swearington |
| 5,065,481 | A | | 11/1991 | Walkhoff |
| 5,065,531 | A | | 11/1991 | Prestridge |
| 5,078,128 | A | | 1/1992 | Grim et al. |
| 5,123,180 | A | | 6/1992 | Nannig et al. |
| 5,125,400 | A | | 6/1992 | Johnson, Jr. |
| D329,527 | S | | 9/1992 | Cohen |
| 5,143,058 | A | | 9/1992 | Luber et al. |
| D330,109 | S | | 10/1992 | Hatfield |
| 5,152,038 | A | | 10/1992 | Schoch |
| 5,154,682 | A | | 10/1992 | Kellerman |
| 5,154,695 | A | | 10/1992 | Farris et al. |
| 5,157,813 | A | | 10/1992 | Carroll |
| 5,176,623 | A | | 1/1993 | Stetman et al. |
| 5,176,624 | A | | 1/1993 | Kuehnreich |
| 5,183,036 | A | | 2/1993 | Spademan |
| 5,197,942 | A | | 3/1993 | Brady |
| D334,646 | S | | 4/1993 | Dissinger |
| D337,876 | S | | 8/1993 | Kilbey |
| 5,233,767 | A | | 8/1993 | Kramer |
| 5,242,379 | A | | 9/1993 | Harris et al. |
| 5,257,470 | A | | 11/1993 | Auger et al. |
| 5,277,695 | A | | 1/1994 | Johnson, Jr. et al. |
| D344,589 | S | | 2/1994 | Kilbey |
| 5,288,286 | A | | 2/1994 | Davis et al. |
| 5,325,613 | A | | 7/1994 | Sussmann |
| 5,329,705 | A | | 7/1994 | Grim et al. |
| 5,352,189 | A | * | 10/1994 | Schumann ............ A61F 5/0111 602/23 |
| D352,191 | S | | 11/1994 | Zorian |
| D352,784 | S | | 11/1994 | Cohen et al. |
| 5,359,791 | A | | 11/1994 | Prahl et al. |
| 5,368,549 | A | | 11/1994 | Mcvicker |
| 5,368,551 | A | | 11/1994 | Zuckerman |
| 5,370,133 | A | | 12/1994 | Darby et al. |
| 5,378,223 | A | | 1/1995 | Grim et al. |
| 5,399,152 | A | | 3/1995 | Habermeyer et al. |
| 5,407,421 | A | | 4/1995 | Goldsmith |
| 5,425,701 | A | | 6/1995 | Oster et al. |
| 5,426,872 | A | | 6/1995 | Hayes |
| 5,429,377 | A | | 7/1995 | Duer |
| 5,429,588 | A | | 7/1995 | Young et al. |
| 5,433,695 | A | | 7/1995 | Drennan |
| 5,435,009 | A | | 7/1995 | Schild et al. |
| 5,438,768 | A | | 8/1995 | Bauerfeind |
| 5,441,015 | A | | 8/1995 | Farley |
| D363,780 | S | | 10/1995 | Darby et al. |
| 5,464,385 | A | | 11/1995 | Grim |
| 5,477,593 | A | | 12/1995 | Leick |
| D365,919 | S | | 1/1996 | Chen |
| 5,483,757 | A | | 1/1996 | Frykberg |

(56) References Cited

U.S. PATENT DOCUMENTS 5,496,263 A 3/1996 Fuller, II et al.
5,548,848 A 8/1996 Huybrechts
D373,548 S 9/1996 Losi, II
5,558,627 A 9/1996 Singer et al.
D375,191 S 11/1996 Tonkel et al.
5,573,501 A * 11/1996 Ruscito ................. A61F 5/0127 602/5
5,577,998 A 11/1996 Johnson, Jr. et al.
D376,429 S 12/1996 Antar
5,617,650 A 4/1997 Grim
D379,258 S 5/1997 Cheng
5,641,322 A 6/1997 Silver et al.
5,647,104 A 7/1997 James
5,656,226 A 8/1997 Mcvicker
D383,250 S 9/1997 Amico
D384,746 S 10/1997 Varn
D390,345 S 2/1998 Aird et al.
5,717,996 A 2/1998 Feldmann
D391,748 S 3/1998 Koh
5,761,834 A 6/1998 Grim et al.
5,778,563 A 7/1998 Ahlbaumer
5,778,565 A 7/1998 Holt et al.
5,797,862 A 8/1998 Lamont
D398,142 S 9/1998 Benoit
D398,439 S 9/1998 Mcdonald
5,819,378 A 10/1998 Doyle
5,827,210 A 10/1998 Antar et al.
5,827,211 A 10/1998 Sellinger
D401,042 S 11/1998 Davis
5,833,639 A 11/1998 Nunes et al.
5,836,902 A 11/1998 Gray
5,846,063 A 12/1998 Lakic
5,853,380 A 12/1998 Miller
5,857,987 A 1/1999 Habermeyer
D404,895 S 2/1999 Rosato
5,868,690 A 2/1999 Eischen, Sr.
5,913,841 A 6/1999 Lamont
5,934,599 A 8/1999 Hammerslag
5,951,504 A 9/1999 Iglesias et al.
5,961,477 A 10/1999 Turtzo
5,993,404 A 11/1999 Mc Niel
6,000,148 A 12/1999 Cretinon
D418,967 S 1/2000 Stengel
6,021,780 A 2/2000 Darby
6,027,468 A 2/2000 Pick
6,044,578 A 4/2000 Kelz
6,098,315 A 8/2000 Hoffmann, III
6,131,195 A 10/2000 Foreman
6,202,953 B1 3/2001 Hammerslag
6,205,685 B1 3/2001 Kellerman
D440,754 S 4/2001 Bathum
6,228,044 B1 5/2001 Jensen et al.
6,267,742 B1 7/2001 Krivosha et al.
RE37,338 E 8/2001 Mcvicker
6,283,932 B1 9/2001 Münch et al.
6,289,558 B1 9/2001 Hammerslag
6,334,854 B1 1/2002 Davis
6,338,768 B1 1/2002 Chi
6,361,514 B1 3/2002 Brown et al.
6,377,178 B1 4/2002 Detoro et al.
6,409,691 B1 6/2002 Dakin et al.
D461,936 S 8/2002 Fiorini et al.
6,432,073 B2 8/2002 Pior et al.
D467,708 S 12/2002 Portzline
6,517,505 B1 2/2003 Veldman
D473,654 S 4/2003 Iglesias et al.
D473,704 S 4/2003 Wilson
6,572,571 B2 6/2003 Lowe
D476,799 S 7/2003 Fuerst
6,589,194 B1 7/2003 Calderon et al.
6,682,497 B2 1/2004 Jensen et al.
6,755,798 B2 6/2004 Mccarthy et al.
6,792,699 B2 9/2004 Long et al.
D500,855 S 1/2005 Pick et al.
6,866,043 B1 3/2005 Davis
D504,005 S 4/2005 Schoenborn et al.
D505,727 S 5/2005 Krahner et al.
6,945,944 B2 9/2005 Kuiper et al.
6,976,972 B2 12/2005 Bradshaw
6,991,613 B2 1/2006 Sensabaugh
D517,306 S 3/2006 Hoeft
7,010,823 B2 3/2006 Baek
7,018,351 B1 3/2006 Iglesias et al.
D523,217 S 6/2006 Matis et al.
D528,214 S 9/2006 Binet
7,198,610 B2 4/2007 Ingimundarson et al.
7,225,564 B1 * 6/2007 Gillespie .................. A43B 3/30 36/35 R
7,281,341 B2 10/2007 Reagan et al.
7,288,076 B2 10/2007 Grim et al.
D554,835 S 11/2007 Peydro
D555,291 S 11/2007 Danzo
D555,343 S 11/2007 Bettencourt
7,303,538 B2 12/2007 Grim et al.
7,311,686 B1 12/2007 Iglesias et al.
D559,988 S 1/2008 Buethorn
7,354,411 B2 4/2008 Perry et al.
RE40,363 E 6/2008 Grim et al.
7,384,584 B2 6/2008 Jerome et al.
D575,039 S 8/2008 Amado et al.
D576,781 S 9/2008 Chang et al.
7,418,755 B2 9/2008 Bledsoe et al.
7,455,651 B2 11/2008 Mollica
D583,544 S 12/2008 Fuerst
D583,956 S 12/2008 Chang et al.
7,493,706 B2 2/2009 Cho et al.
7,524,295 B1 4/2009 Peters et al.
D592,755 S 5/2009 Chang et al.
D592,756 S 5/2009 Chang et al.
D594,368 S 6/2009 Butler
D596,301 S 7/2009 Campos et al.
D596,386 S 7/2009 Brambilla
7,591,050 B2 9/2009 Hammerslag
D603,155 S 11/2009 Della Valle et al.
D614,775 S 4/2010 Snively
D615,285 S 5/2010 Martin
D616,556 S 5/2010 Hu
7,717,869 B2 5/2010 Eischen, Sr.
7,727,174 B2 6/2010 Chang et al.
D622,494 S 8/2010 Warren
7,838,717 B2 11/2010 Haggstrom et al.
D634,438 S 3/2011 Hu
D634,852 S 3/2011 Hu
D636,157 S 4/2011 Nascimento
D636,159 S 4/2011 Petrie
7,964,766 B2 6/2011 Blott et al.
D642,363 S 8/2011 Rajmohan et al.
D642,775 S 8/2011 Raysse
8,002,724 B2 8/2011 Hu et al.
8,012,112 B2 9/2011 Barberio
8,021,347 B2 9/2011 Vitaris et al.
D648,113 S 11/2011 Chang
RE43,063 E 1/2012 Kim
D651,381 S 1/2012 Simms
8,158,844 B2 4/2012 Mcneil
D661,887 S 6/2012 Petrie
8,308,705 B2 11/2012 Lin et al.
8,313,449 B2 11/2012 Hardman et al.
D675,421 S 2/2013 Petrie
D677,866 S 3/2013 Vestuti et al.
D680,728 S 4/2013 Stryjak
D682,517 S 5/2013 Taylor
D683,214 S 5/2013 Mcadam
D684,760 S 6/2013 Williams, Jr.
8,506,510 B2 8/2013 Hu et al.
D689,677 S 9/2013 Bathum et al.
8,574,181 B2 11/2013 Bird et al.
D696,499 S 12/2013 Lehtinen
D696,785 S 12/2013 Weaver, II et al.
D698,074 S 1/2014 Hargreaves
D698,338 S 1/2014 Ingham et al.
D700,404 S 2/2014 Niefer
D701,032 S 3/2014 Leleu
D701,033 S 3/2014 Leleu

(56) References Cited

U.S. PATENT DOCUMENTS

| | | | |
|---|---|---|---|
| D703,335 | S | 4/2014 | Bird et al. |
| D709,277 | S | 7/2014 | Takenaka |
| D712,639 | S | 9/2014 | Spring |
| D714,042 | S | 9/2014 | Petrie |
| 9,003,677 | B2 | 4/2015 | Goodsmith et al. |
| D729,393 | S | 5/2015 | Dunn et al. |
| D740,896 | S | 10/2015 | Halper, Jr. |
| D742,017 | S | 10/2015 | Dunn et al. |
| D744,111 | S | 11/2015 | Dunn et al. |
| 9,220,621 | B2 | 12/2015 | Hu et al. |
| 9,220,622 | B2 | 12/2015 | Ingimundarson et al. |
| 9,248,042 | B2 | 2/2016 | Lopez et al. |
| 9,333,106 | B2 | 5/2016 | Hu et al. |
| 9,375,340 | B2 | 6/2016 | Batterson et al. |
| 9,468,553 | B2 | 10/2016 | Hu et al. |
| 9,474,334 | B2 | 10/2016 | Jonsson et al. |
| D772,418 | S | 11/2016 | Dunn et al. |
| 9,492,301 | B2 | 11/2016 | Hu et al. |
| D776,288 | S | 1/2017 | Dunn et al. |
| D776,289 | S | 1/2017 | Dunn et al. |
| 9,668,907 | B2 | 6/2017 | Romo et al. |
| 9,744,065 | B2 | 8/2017 | Walborn et al. |
| 9,839,548 | B2 | 12/2017 | Ingvarsson et al. |
| 9,839,549 | B2 | 12/2017 | Walborn et al. |
| 9,839,550 | B2 | 12/2017 | Walborn et al. |
| 10,667,939 | B2 | 6/2020 | Kim |
| 10,702,413 | B2 | 7/2020 | Kim |
| 2002/0095105 | A1 | 7/2002 | Jensen |
| 2002/0095750 | A1 | 7/2002 | Hammerslag |
| 2002/0128574 | A1 | 9/2002 | Darby |
| 2003/0093882 | A1 | 5/2003 | Gorza et al. |
| 2003/0171703 | A1 | 9/2003 | Grim et al. |
| 2003/0204938 | A1 | 11/2003 | Hammerslag |
| 2004/0010212 | A1 | 1/2004 | Kuiper et al. |
| 2004/0019307 | A1 | 1/2004 | Grim et al. |
| 2004/0167453 | A1 | 8/2004 | Peters |
| 2005/0060914 | A1 | 3/2005 | Fuerst |
| 2005/0131324 | A1 | 6/2005 | Bledsoe |
| 2005/0145256 | A1* | 7/2005 | Howard ................ A61F 5/0111 128/882 |
| 2005/0165338 | A1 | 7/2005 | Iglesias et al. |
| 2005/0171461 | A1* | 8/2005 | Pick ........................ A61F 5/012 602/27 |
| 2005/0172517 | A1 | 8/2005 | Bledsoe et al. |
| 2005/0187505 | A1 | 8/2005 | Carlson |
| 2005/0274046 | A1 | 12/2005 | Schwartz |
| 2006/0048344 | A1 | 3/2006 | Cavanagh et al. |
| 2006/0084899 | A1 | 4/2006 | Verkade et al. |
| 2006/0135899 | A1 | 6/2006 | Jerome et al. |
| 2006/0135902 | A1 | 6/2006 | Ingimundarson et al. |
| 2006/0156517 | A1 | 7/2006 | Hammerslag et al. |
| 2006/0189907 | A1 | 8/2006 | Pick et al. |
| 2006/0217649 | A1 | 9/2006 | Rabe |
| 2006/0229541 | A1 | 10/2006 | Hassler et al. |
| 2007/0011914 | A1 | 1/2007 | Keen et al. |
| 2007/0055188 | A1 | 3/2007 | Avni et al. |
| 2007/0167884 | A1 | 7/2007 | Mangrum et al. |
| 2007/0169378 | A1 | 7/2007 | Sodeberg et al. |
| 2007/0185425 | A1 | 8/2007 | Einarsson et al. |
| 2007/0191749 | A1 | 8/2007 | Barberio |
| 2007/0282230 | A1 | 12/2007 | Valderrabano et al. |
| 2007/0293798 | A1* | 12/2007 | Hu ........................ A61F 5/0195 602/27 |
| 2008/0060167 | A1 | 3/2008 | Hammerslag et al. |
| 2008/0060168 | A1 | 3/2008 | Hammerslag et al. |
| 2008/0066272 | A1 | 3/2008 | Hammerslag et al. |
| 2008/0066345 | A1 | 3/2008 | Hammerslag et al. |
| 2008/0066346 | A1 | 3/2008 | Hammerslag et al. |
| 2008/0083135 | A1 | 4/2008 | Hammerslag et al. |
| 2008/0294082 | A1 | 11/2008 | Chang et al. |
| 2008/0294083 | A1 | 11/2008 | Chang et al. |
| 2008/0319362 | A1 | 12/2008 | Joseph |
| 2009/0012482 | A1 | 1/2009 | Pinto et al. |
| 2009/0099495 | A1 | 4/2009 | Campos et al. |
| 2009/0227927 | A1 | 9/2009 | Frazer |
| 2009/0234260 | A1 | 9/2009 | Coward et al. |
| 2009/0270820 | A1 | 10/2009 | Johnson et al. |
| 2009/0287127 | A1 | 11/2009 | Hu et al. |
| 2009/0287128 | A1 | 11/2009 | Ingimundarson et al. |
| 2010/0069808 | A1 | 3/2010 | Mitchell |
| 2010/0100020 | A1 | 4/2010 | Fout et al. |
| 2010/0234782 | A1 | 9/2010 | Hu et al. |
| 2010/0287793 | A1 | 11/2010 | Hall et al. |
| 2010/0324461 | A1 | 12/2010 | Darby, II et al. |
| 2011/0009791 | A1 | 1/2011 | Hopmann |
| 2011/0015555 | A1 | 1/2011 | Anderson et al. |
| 2011/0016750 | A1* | 1/2011 | Crowley, II ......... A43B 3/0052 36/103 |
| 2011/0196275 | A1 | 8/2011 | Chang et al. |
| 2012/0010534 | A1 | 1/2012 | Kubiak et al. |
| 2012/0035560 | A1 | 2/2012 | Eddy et al. |
| 2012/0078148 | A1 | 3/2012 | Hu et al. |
| 2012/0130292 | A1 | 5/2012 | Benjoar |
| 2012/0220960 | A1 | 8/2012 | Ruland |
| 2012/0238924 | A1 | 9/2012 | Avni |
| 2013/0018294 | A1* | 1/2013 | Jones ........................ A61F 5/30 602/27 |
| 2013/0066247 | A1* | 3/2013 | Bird ...................... A61F 5/0111 602/27 |
| 2013/0310721 | A1 | 11/2013 | Hu et al. |
| 2014/0039368 | A1 | 2/2014 | Perkins |
| 2014/0128789 | A1 | 5/2014 | Chen |
| 2014/0171837 | A1 | 6/2014 | Harcourt |
| 2014/0265018 | A1 | 9/2014 | Grim et al. |
| 2014/0276310 | A1 | 9/2014 | Grim et al. |
| 2014/0350446 | A1 | 11/2014 | Gunnsteinsson |
| 2015/0075030 | A1 | 3/2015 | Walborn et al. |
| 2015/0088046 | A1* | 3/2015 | Walborn ............... A61F 5/0195 602/27 |
| 2015/0164179 | A1 | 6/2015 | Walborn et al. |
| 2016/0000174 | A1 | 1/2016 | Grim et al. |
| 2016/0015121 | A1* | 1/2016 | Romo .................. A43B 17/006 36/43 |
| 2016/0213823 | A1 | 7/2016 | Walborn et al. |
| 2017/0216078 | A1 | 8/2017 | Rivlin et al. |
| 2017/0296373 | A1 | 10/2017 | Bean et al. |
| 2019/0076286 | A1 | 3/2019 | Kim |
| 2019/0142622 | A1 | 5/2019 | Kim |
| 2019/0240057 | A1* | 8/2019 | Gunnsteinsson ..... A61F 5/0111 |

FOREIGN PATENT DOCUMENTS

| | | | |
|---|---|---|---|
| CN | 104736109 | A | 6/2015 |
| DE | 23 416 58 | A1 | 3/1974 |
| DE | 32 287 53 | A1 | 2/1984 |
| DE | 9314920 | U1 | 3/1994 |
| EP | 0 095 396 | A1 | 11/1983 |
| EP | 0 201 051 | A1 | 11/1986 |
| EP | 0770368 | A1 | 5/1997 |
| EP | 1238640 | A1 | 9/2002 |
| EP | 2147664 | A1 | 1/2010 |
| EP | 2468323 | A1 | 6/2012 |
| EP | 3431056 | A1 | 1/2019 |
| FR | 2 399 811 | A1 | 3/1979 |
| FR | 2634988 | A1 | 2/1990 |
| FR | 2 681 516 | A1 | 3/1993 |
| GB | 2 124 473 | A | 2/1984 |
| GB | 2 178 940 | A | 2/1987 |
| JP | 2005211626 | A | 8/2005 |
| KR | 101243558 | B1 | 3/2013 |
| KR | 20150019768 | A | 2/2015 |
| KR | 101694792 | B1 | 1/2017 |
| KR | 101694805 | B1 | 1/2017 |
| WO | 93/13685 | A1 | 7/1993 |
| WO | 93/24081 | A1 | 12/1993 |
| WO | 94/18863 | A1 | 9/1994 |
| WO | 97/36507 | A1 | 10/1997 |
| WO | 2004/021817 | A1 | 3/2004 |
| WO | 2006035469 | A2 | 4/2006 |
| WO | 2006045079 | A1 | 4/2006 |
| WO | 2007078845 | A2 | 7/2007 |
| WO | 2010104824 | A1 | 9/2010 |
| WO | 2013/084213 | A1 | 6/2013 |

(56) References Cited

FOREIGN PATENT DOCUMENTS

| | | |
|---|---|---|
| WO | 2014032029 A1 | 2/2014 |
| WO | 2015006766 A1 | 1/2015 |
| WO | 2017160064 A1 | 9/2017 |

OTHER PUBLICATIONS

Product Information Sheet: XP Walker (extra pneumatic), Aircast, Jan. 1, 2008, 4 pages. Retrieved from the Internet, http://www.aircast.com/index.asp/fuseaction/products.detail/cat/2/id/76.
Product Information Sheet: Nextep Contour Walker, Procare, DJ Orthopedics, Jan. 1, 2008, 1 page. Retrieved from the internet, www.djortho.com.
Product Information Sheet: Nextep Contour w/Air Walker, Procare, DJ Orthopedics, Jan. 1, 2008, 1 page. Retrieved from internet, www.djortho.com.
Product Information Sheet: XP Achilles Walker (EU only), Aircast, Jan. 1, 2008, 4 pages. Retrieved from the Internet, http://www.aircast.com/index.asp/fuseaction/products.detail/cat/2/id/104.
Product Information Sheet: XP Diabetic Walker System, Aircast, Jan. 1, 2008, 4 pages. Retrieved from the Internet, http://www.aircast.com/index.asp/fuseaction/products.detail/cat/2/id/15.
Product Information Sheet: SP Walker (short pneumatic), Aircast, Jan. 1, 2008, 4 pages. Retrieved from the internet, http://www.aircast.com/index.asp/fuseaction/products.detail/cat/2/id/14.
Product Information Sheet: FP Walker (foam pneumatic), Aircast, Jan. 1, 2008, 4 pages. Retrieved from the Internet, http://www.aircast.com/index.asp/fuseaction/products.detail/cat/2/id/75.
"Eva Explained, What Is It?," Monmouth Rubber & Plastics, as early as Dec. 31, 2019, 4 Pages.
Hanhi et al., "Elastomeric Materials," Tampere University of Technology, The Laboratory of Plastics and Elastomer Technology, as early as Dec. 31, 2007, 84 Pages.
"Aircast AirSelect Standard Patient Information," DJO Global, as early as Dec. 31, 2013, 1 Page.
"FP Walker Foam Pneumatic," Aircast, 2 Pages, Downloaded on Feb. 4, 2019.
"Airselect Standard," DJO, Downloaded from https://www.djoglobal.com/products/aircast/airselect-standard, as early as Dec. 31, 2019, 4 Pages.
"Genesis Walker The lightest Full Shell Walker Boot on the Market," Breg Inc, as early as Dec. 31, 2015, 6 Pages.
"FP Walker (Foam Pneumatic)," DJO, Downloaded from https://www.djoglobal.com/products/aircast/fp-walker-foam-pneumatic, as early as Dec. 31, 2019, 4 Pages.
"Rebound Air Walker the Standard in Foot and Ankle Care," Ossur, at least by Mar. 31, 2016, 4 Pages.
"Townsend XLR8 Pneumatic Walker," Townsend AThuasne Company, downloaded from www.townsenddesign.com on Feb. 4, 2019, 4 Pages.
International Search Report and Written Opinion from PCT Application No. PCT/US2021/059657, Nov. 17, 2021.
Partial International Search Report from PCT Application No. PCT/US2021/059657, Feb. 16, 2022.
Foam Factory, Polyethylene Foam: Its Uses, Characteristics, and Varieties, Nov. 9, 2011, https://www.foambymail.com/ blog/polyethylene-foam-its-uses-characteristics-and-varieties/#:~:text=Polyethylene%20is%20closed%2Dcell%20foam,present%20in%20open%2Dcell%20foams.
Foamsealant, What is an EVA foam and its common uses, May 25, 2015, https://foamsealant.com.au/what-is-an-eva-foam-and-its-common-uses/.
Office Action from corresponding Chinese Application No. 201980011136.3, Dec. 2, 2021.
Office Action from corresponding Chinese Application No. 201980011136.3, Jul. 21, 2022.
Chinese Office Action from Corresponding Chinese Patent Application No. CN202180076997.7, Nov. 15, 2025.

* cited by examiner

FIG. 24A
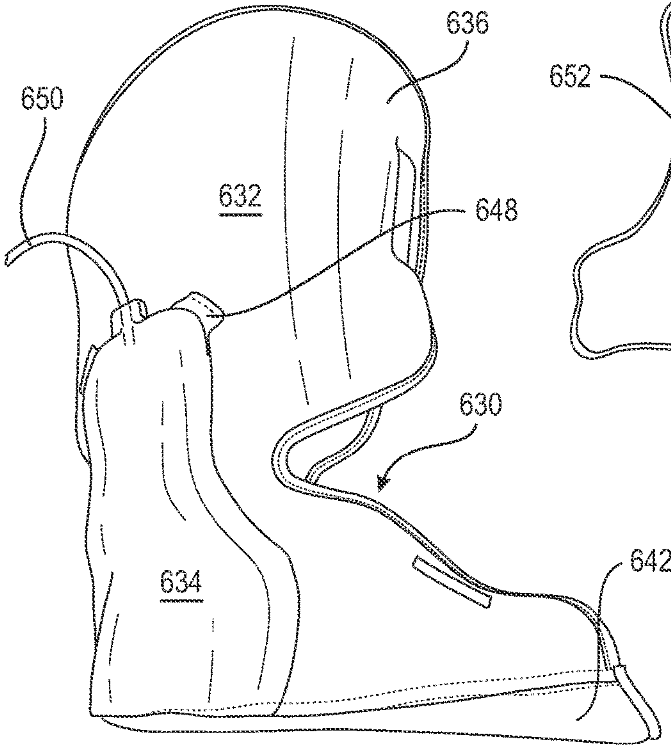
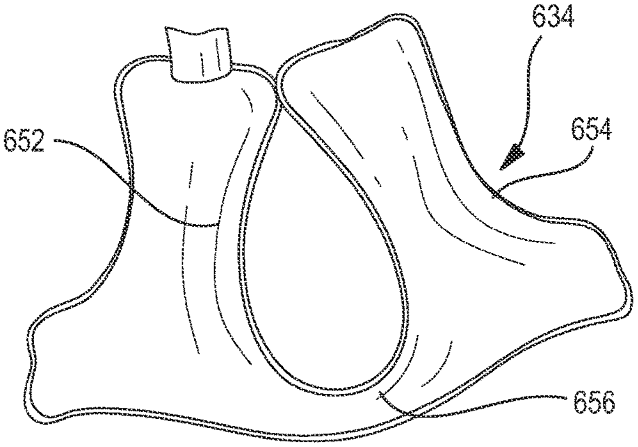
FIG. 24C
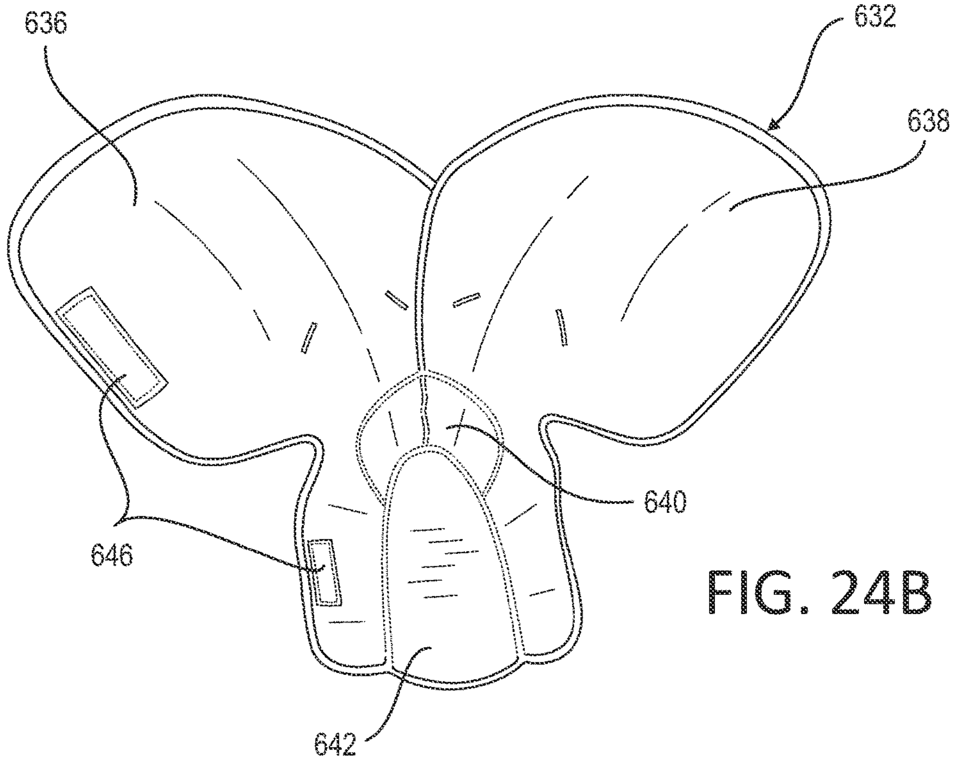
FIG. 24B

ORTHOPEDIC WALKER

CROSS-REFERENCE TO RELATED APPLICATIONS

This application incorporates by reference U.S. application Ser. No. 16/266,925, filed on Feb. 4, 2019, and U.S. provisional application No. 63/213,391, filed Jun. 22, 2021, and U.S. provisional application No. 63/115,804, filed Nov. 19, 2020.

BACKGROUND

Sprains, fractures, and soft tissue injuries involving the lower leg and foot commonly result from household accidents, workplace incidents, and sports-related trauma. Other wounds or sensitive areas in the lower limbs may result from surgical intervention or the effect of certain medical conditions. These injuries affect a broad range of individuals and, while not life-threatening, can increase in severity without treatment, stabilization, and/or protection.

Prior art solutions for treating, stabilizing, and/or protecting the lower limb after injury or surgery can be categorized into two approaches: casting systems and orthopedic braces. Each approach can provide the required rigid support to a user's limb, with distinct disadvantages and drawbacks.

Known casting systems are typically fabricated directly on a user's limb and conform to the unique anatomy. The casting systems comprise an interior padding and an exterior layer of materials moldable in a first state before transitioning into a rigid material state, e.g., molded plasters or resins applied to a limb and then hardened in place. The casting systems are often difficult and messy to create, are not adjustable once hardened, are not easily removed without being destroyed, are not reusable, are not breathable or hygienic, and must be worn for long, uninterrupted periods.

Orthopedic braces include a wide range of splints, braces, and walking boots. The braces can be mass-produced and form complex multi-component systems that allow adjustment or tightening to a user's limb. Such multi-component systems often include several straps or other securing means, with rigid plastic shells or splints for securing a padded structure around a limb, enclosing or wrapping the limb in both a soft or padded internal covering, with a harder frame or external shell. The complexity of the multi-component systems and the cost of the required materials render orthopedic braces uneconomical for personalized construction conforming to the anatomy or treatment needs.

There is a need for a stabilizing solution adaptable to a user's anatomy at a low cost, and that is adjustable about the limb of a user, with fewer or no complex multi-component systems.

Further, both the unadaptable casting systems and the complex orthopedic braces are bulky and heavy. Many conventional walkers are at least 750 grams, and many are at least 850 g. The exterior surface of a cast may be rough, while the surface profile of an orthopedic brace is uneven, and each can frequently disrupt the use of clothing, furniture, and bedding or cause uncomfortable contact against another limb of the user. There is a further need for a more comfortable solution around the limb and lighter and streamlined in construction, and more convenient in use.

An additional challenge in existing devices, including conventional strut walkers, is the unyielding, uncomfortable, and inconvenient nature of existing immobilization techniques. For example, conventional strut walkers comprise a footplate and two unyielding struts (frequently metal) arranged with a shell to immobilize a portion of a user's anatomy. The unyielding characteristics of conventional devices, provided for immobilization, yield a device that is difficult to adapt to a user's individual needs and dimensions, especially around the lower leg, particularly because existing devices are often provided based on a user's shoe size but not based on the size of their lower leg. There is a need for a device that provides needed immobilization while minimizing the challenges presented by the unyielding nature of existing devices.

Users find orthopedic walkers uncomfortable due to leg length discrepancies between the healthy leg and the impaired leg donning the walker. Most orthopedic walkers have a heel height of at least 34 mm due to the need to cushion and stabilize the heel. The height results from the multiple layers and thickness required to stabilize the heel. A slight difference in midsole and heel height can cause problems with the user's gait and contribute to the lower back, hip, ankle, and knee pain.

The disclosure's orthopedic walker or walking boot bridges the gap between the two prior art solutions, providing the advantages of a solution adjustably conforming to the individual anatomy and without the related drawbacks of added weight, complexity, and cost.

SUMMARY

An orthopedic walker or walking boot is arranged with a construction to facilitate donning and doffing and provide a limb with reliable protection and support.

The walker may be configured as having a semi-rigid body material to reduce the walker's complexity, cost, and weight. The semi-rigid nature of the body material provides rigid support to the limb and allows the walker to resiliently hold or return to its original shape while having flexibility or resiliency to facilitate regular and comfortable donning and doffing. While a semi-rigid body material is preferable, other materials are envisioned.

The walker combines a casting system's strength, support, and customized fit with an orthopedic brace's adjustability and other functional and structural advantages. Due to semi-rigid body material, the walker may be advantageously manufactured with a unitary form construction or a single-part construction or multiple components. The semi-rigid body material may preferably constitute a unitary construction to provide a comfortable and readily adjustable fit about a limb with no additional splints, supports, padding, or other components as required in prior art devices. The semi-rigid body material further reduces the walker's cost and weight relative to casting systems and conventional orthopedic braces.

Material properties of the walker's body can be adjusted to accommodate the desired fit and hold of the walker. Increased elasticity can urge the walker body towards a closed position over a limb, helping to secure the walker on a user's limb during periods of activity. Increased rigidity can be used for injuries where protection from external forces is most important and/or provided in regions requiring greater immobilization or support.

The walker body can be advantageously configured with a smooth, streamlined, and soft surface both on the walker's interior and exterior surfaces while retaining enough strength to stabilize the limb. The smooth surface prevents the walker from catching on clothing or other objects such as knee scooters or crutches or causing discomfort during sleep or other activities.

The walker's body's streamlined appearance and profile offer a less bulky design, more closely approximating a sneaker or athletic shoe. Because of aesthetic appearance and tighter fitting result due to less bulk and a more tailored interior volume to a user's leg and foot, it is estimated that better compliance in wearing the orthopedic walker may be achieved.

Unlike in known walkers, the tread of the outsole is formed unitarily and integrated with the rest of the body of the walker, negating a need to adhere a separate outsole tread to the walker. This arrangement offers significant benefits in lowering the heel and midsole heights of the walker to more closely approximate the heel height of the unimpaired foot relative to the ground, whether in a shoe or without a shoe. The outsole tread may be formed to have a slip-resistant pattern or otherwise adapted (i.e., recesses, protrusions) to avoid slipping on a ground surface.

The material used in the walker body may be selected based on the needs of individual users and/or activity levels. A thicker or higher density material may be used for more active users, while a thinner or lower density material may be used for less active users. The variation of material properties of the walker body may be adjusted based on the injury of a user and the user's activity level and can treat many injuries and users.

Similarly, embodiments described may herein use varying material properties, including different thicknesses, densities, or hardnesses of body material, to adjust the flexibility and resiliency of different portions of the walker about a limb. Injured areas may receive greater support, compression, immobilization, or protection, while other areas provide increased mobility and comfort.

An exemplary body material may be an expanded plastic. By understanding expanded plastic, it is understood that the plastic may be porous or foam-like, such as closed-cell. The expanded plastic may be selected due to its stiffness, either in the material composition or structurally, such as by thickness, or according to both. An example of an expanded plastic is ethylene-vinyl acetate (EVA), an expanded rubber or foam rubber, and an elastomeric polymer that produces materials with rubber-like softness flexibility. The EVA may have different proportions of vinyl-acetate, which structurally may modify the toughness and stiffness of the EVA. Other polymeric materials may form the body and be selected from the non-limiting group comprising polyurethane, polyethylene, and polypropylene.

The expanded plastic offers a stiff but lighter body than conventional orthopedic walkers. The expanded plastic also allows for flexibility that facilitates donning of the walker. Donning and doffing of the unitary form walker may be facilitated by at least one opening provided in the walker body, which may be in an elongate opening or another form. The at least one opening may be configured to partially divide the walker body into a first and second sides along a limb-receiving region of the walker. The at least one opening may extend along the limb-receiving region's length to allow a user to fold back the first and second sides of the walker to insert a limb into the limb-receiving region without excessive bending of an injured limb or joint. This arrangement may advantageously provide for easier donning from a supine position, e.g., post-surgery.

The at least one opening may also be configured to allow access to the limb while the walker body is secured to a limb. The walker body may secure a user's ankle while also having an elongate opening exposing a proximal side of a foot and toes. Such a configuration allows a clinician to access bandaging about the foot, allows additional space for injured toes, and/or ventilates the proximal side of the foot without sacrificing needed stability, immobilization, or support.

These and other features, aspects, and advantages of the present disclosure will better understand the following description, appended claims, and drawings.

BRIEF DESCRIPTION OF THE DRAWINGS

The drawing figures are not necessarily drawn to scale but instead are drawn to provide a better understanding of the components thereof and are not intended to be limiting in scope but to provide exemplary illustrations. The figures illustrate exemplary configurations of an orthopedic walker and in no way limit the structures or configurations according to the present disclosure.

FIG. 24A is a perspective view of a softgood and bladder assembly for insertion into the orthopedic walker of FIG. 20A.

FIG. 24B is a perspective view of a bladder of the softgood and bladder assembly of FIG. 24A.

FIG. 24C is a perspective view of a softgood of the softgood and bladder assembly of FIG. 24A.

DETAILED DESCRIPTION OF VARIOUS EMBODIMENTS

A. Introduction of Embodiments and Definitions of Terms

Embodiments of an orthopedic walker are used for donning and doffing on a user and are provided for stabilizing and supporting anatomical portions of a user, for example, the lower leg, ankle, and foot of a user.

The walker has a semi-rigid or rigid body material to reduce the walker's complexity, cost, and weight. The semi-rigid nature of the body material provides rigid support when worn on the limb and allows the walker to resiliently hold or return to its original shape while having flexibility or resiliency to facilitate regular donning doffing. Unlike conventional orthopedic walkers, a preferred embodiment of the walker body is constructed from a single material and obviates the necessity of providing different structural materials. The walker eliminates the need for securing different materials with adhesives and fasteners and has enough strength and resiliency to withstand normal ground reaction forces incurred on the foot, ankle, and leg while stabilizing the limb and offering an intimate fit. However, it is envisioned that the orthopedic walker need not be solely limited to the unitary construction.

The walker combines the strength and support of a casting system with the adjustability of an orthopedic walker. However, the walker may be advantageously manufactured with a unitary form construction or a single part construction due to semi-rigid body material. The simplified construction enhances ease and comfort of use and offers a more lightweight structure.

Although the embodiments of the disclosure are suitable for supporting and stabilizing anatomical portions of many users having various anatomical shapes and sizes, the embodiments of the disclosure may also be dimensioned to accommodate different types, shapes, and sizes of anatomical portions. The walker may be an off-the-shelf product accommodating general sizes and shapes of the lower limb and feet or may be readily custom fabricated.

It will be understood that, unless a term is defined in this disclosure to possess a described meaning, there is no intent to limit the meaning of such term, either expressly or indirectly, beyond its plain or ordinary meaning.

Figure 1:
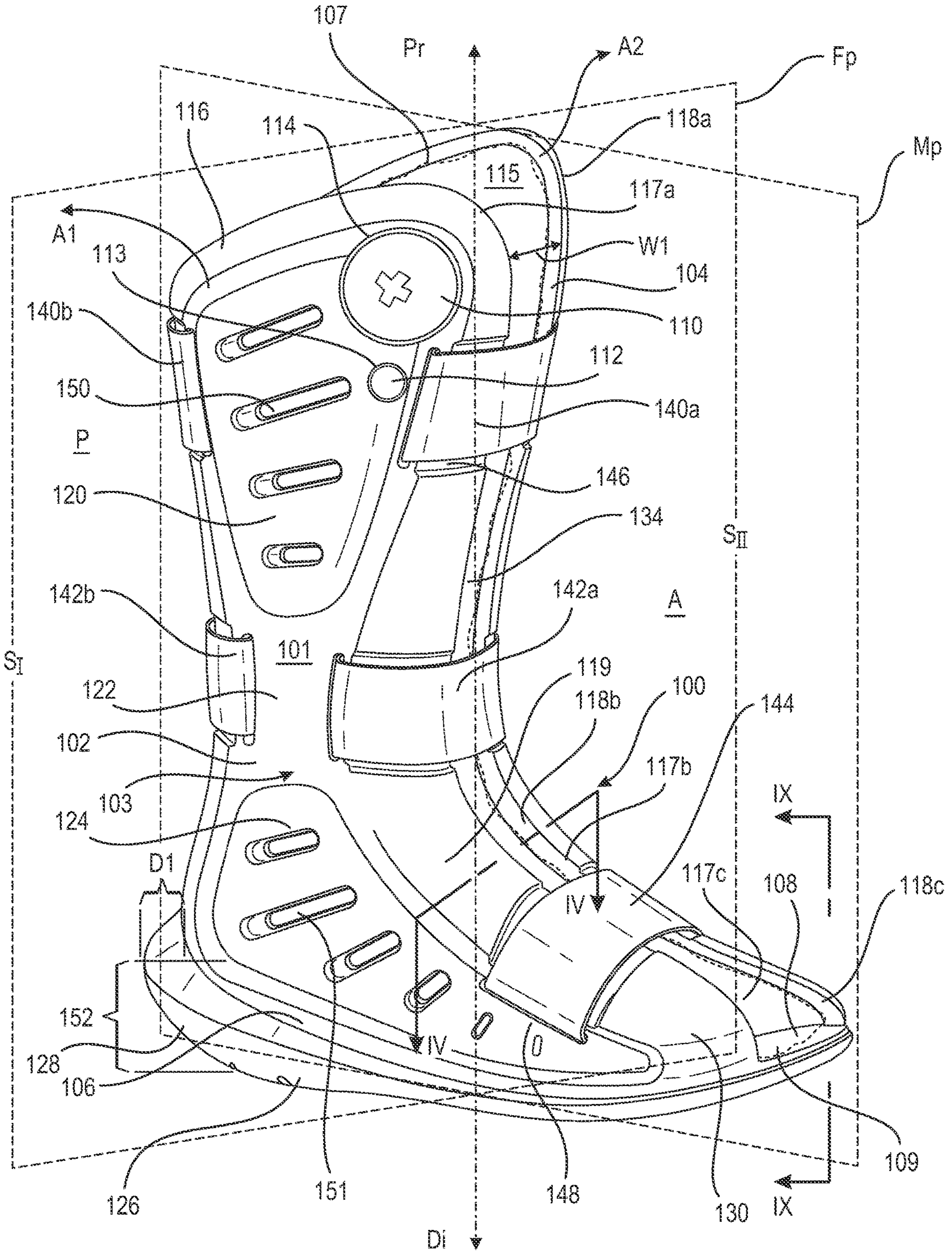
FIG. 1 is a perspective side view of an embodiment of an orthopedic walker.

While the foregoing embodiments have been described and shown, alternatives and modifications of these embodiments, such as those suggested by others, may be made to fall within the disclosure. While the orthopedic walker has been described with a shape conforming to a lower leg and foot, it will be understood that the principles described may be extended to other types of orthopedic devices and/or for other limbs or body portions For ease of understanding, the disclosed embodiments of an orthopedic walker, the front or anterior, and rear or posterior portions of the orthopedic walker are described independently. The anterior and posterior portions are defined by a frontal or coronal plane, $F_p$, as depicted in FIG. 1. The anterior and posterior portions of the orthopedic walker function together to form a supporting and stabilizing boot that encompasses the user's anatomical portions.

For some embodiments, the lateral and medial portions of the orthopedic walker are described independently. The lateral and medial portions are defined by a median or sagittal plane, $M_p$, as depicted in FIG. 1. The lateral and medial portions of the orthopedic walker function together to form a supporting and stabilizing boot that encompasses the user's anatomical portions. When the orthopedic walker is universal or generally symmetric for both right and left legs and feet, the sides of the orthopedic walker SI, Su, are divided by the median plane, as shown in at least FIG. 1.

The term "posterior" also has its ordinary meaning and refers to a location behind or to the rear of another location. The term "anterior" has its ordinary meaning and refers to a location ahead of or in front of another location. The term "medial" has its ordinary meaning and refers to a location near the median plane, such as the inside of a foot. The term "lateral" has its ordinary meaning and refers to a location farther from the median plane, such as the outside of a foot.

The term "distal" has its ordinary meaning and refers to a location farther from the point of attachment of a limb. The term "proximal" has its ordinary meaning and refers to a location closer to the point of attachment. However, a structure can be proximal or distal about another point of reference. A knee is distal to an upper leg but proximal to the lower leg; however, in the orthopedic walker context, the knee is a frame of reference such that proximal $P_r$ is closer to the knee and whereas distal $D_i$ is farther from the knee.

The terms "rigid," "semi-rigid," and "compressible" may distinguish characteristics of portions of certain features of the orthopedic walker. The term "rigid" should denote that an element of the device is devoid of flexibility. Within the context of support members or shells that are "rigid," it should indicate that they do not lose their overall shape when force is applied, and they may break if bent with enough force.

As for the term "semi-rigid," this term is generally used to connote properties of support members that provide support and are free-standing; however, such support members have flexibility or resiliency and may continuously deform when appropriate force is applied. The term "compressible" may generally qualify such structural features as being capable of being reduced in size or volume due to the exertion of force applied to the structural feature. The "expanded" plastic may have a lightweight cellular structure, such as a closed-cell foam; however, the expanded plastic may cover a porous material or other generally lightweight or low-density material.

The term "unitary" may generally denote that an element of the walker is continuous in its construction instead of comprising an assemblage of separate and spatially adjustable components. The term "elongate" may generally denote that an element of the walker is longer than it is wide.

A better understanding of different embodiments of the disclosure may be had from the following description read with the drawings in which reference characters refer to like elements. While the disclosure is susceptible to various modifications and alternative constructions, certain illustrative embodiments are in the drawings and are described below. It should be understood; however, there is no intention to limit the disclosure to the embodiments disclosed, but on the contrary, the intention covers all modifications, alternative constructions, combinations, and equivalents falling within the spirit and scope of the disclosure.

B. Description of Embodiments

FIG. 1 shows a perspective view of an orthopedic walker 100 in a closed configuration, meaning it is in a predetermined configuration available for donning and adjustment for an individual user. The orthopedic walker 100 has a body 101 formed by a unitary form construction, wherein the body 101 is formed from the same material and arranged to extend about a user without interruption, and the structure of the body 101 consists of a single material part including various features available to support extraneous features.

The extraneous features to the unitary form construction of the body may include a pump 110 and valve 112 adapted to communicate with a liner 107 having a bladder arranged to line an interior volume 105 along the interior surface 111 of the body 101. Straps 140, 142, 144 may be connected to the body 101 and have features permitting attachment thereto. Some of such straps preferably form a circumference with the body for surrounding a user's lower leg.

The body 101 has a shape corresponding to a limb and having a unitary form construction to fit against the user intimately. The body 101 is configured to receive a limb of a user in an open configuration, as illustrated in U.S. application Ser. No. 16/266,925, and to close about the limb of the user in a closed configuration, as illustrated in FIG. 1. In the closed configuration of FIG. 1, the body 101 may have the general shape of a boot, conforming to the shape of a user's foot and a portion of a user's lower leg, inclusive of the ankle. While in the general shape of a boot, the footprint and bulk of the orthopedic walker 100 is streamlined as it is contoured to the general shape of a lower leg and foot. As discussed, advantages include reducing the height and midsole height because the body 101 has a unitary form construction and may not necessitate different layers and corresponding adhesives and interlocking portions (metal struts, outsole treads, etc.) as in a conventional walker. Both the exterior and interior surfaces/peripheries 103, 111 of the body 101 are substantially form-fitting to the anatomical shape of a lower leg and foot.

The body 101 may be configured to an intended treatment purpose for the user. The height of the body 101 may vary depending on the condition to be treated, yet the height at the footbed 106 relative to the ground and the unimpaired foot and leg of the user may be more closely approximated than conventional walkers. The body 101 may have a high top extending up the user's lower leg or manufactured or trimmed to have a low top. The orthopedic walker 100 may be configured in different heights to accommodate the pathologies and indications used for treatment.

Due to the unitary construction of the orthopedic walker 100, the body 101 may have an open or closed-toe region 108. A closed toe configuration may be advantageous over prior art embodiments of a cast, where a closed toe is only possible by tightly wrapping the toe area, and an orthopedic brace, where the toe is left open due to the constraints of a multi-component system. The open toe configuration may be advantageous for providing increased access, space, and/or ventilation to the limb of the user. Advantageously, the body 101 may be configured to the needs of the user, and/or may be cut or otherwise altered to adapt to the needs of the user.

However, as shown and discussed with FIGS. 11 and 12, toe cover means may be provided to address closing the toe region 108 without interfering with the open toe region of the body 101. The orthopedic walker 100 may be provided with a closed-toe region 108 due to the ability to mold the closed-toe region with the material of the body 101 itself, as shown and discussed with FIG. 13.

The body 101 may be formed as a single part from a semi-rigid body material. The semi-rigid body material reduces the complexity, cost, and weight of the orthopedic walker 100. The semi-rigid nature of the body material provides rigid support to the limb and allows the orthopedic walker 100 to resiliently hold or return to its original shape while having flexibility or resiliency to facilitate regular donning and doffing. Preferred materials for forming the body 101 include an expanded polymer such as EVA, rubber foam, or closed-cell foam. Alternate polymeric materials may be employed, having enough rigidity to intimately support and hold the lower limb and foot while offering a protective barrier to elements and enabling the body 101 to likewise serve as the sole being subjected to repeated ground strikes. The materials for forming the body 101 may also advantageously reduce the bodyweight of the orthopedic walker 100 without sacrificing needed robustness.

The semi-rigid body material may be configured to have distinct material properties, including material thickness, densities, etc., according to a preferred treatment and/or stabilization. The semi-rigid body material may be configured to substantially retain a shape of a closed configuration of the body 101. In some embodiments, the semi-rigid body material may be configured such that the body 101 provides compression for securing the body 101 about the limb when no force or pressure is applied to the body 101. A shape of the body 101 may be configured to support a particular area or prevent a particular limb's particular motion.

The interior volume 105 of the orthopedic walker 100 and the body 101 may be defined by first and second portions 102, 104 defining an upper or proximal part of the orthopedic walker 100 corresponding to the lower leg, and a footbed 106 defining a lower or distal part of the orthopedic walker 100 corresponding to the foot of a user. As a preferred material for forming the body 101 is a structural foam, the body 101 may be directly secured against the limb while offering rigidity and compressive support without discomfort.

Figure 10:
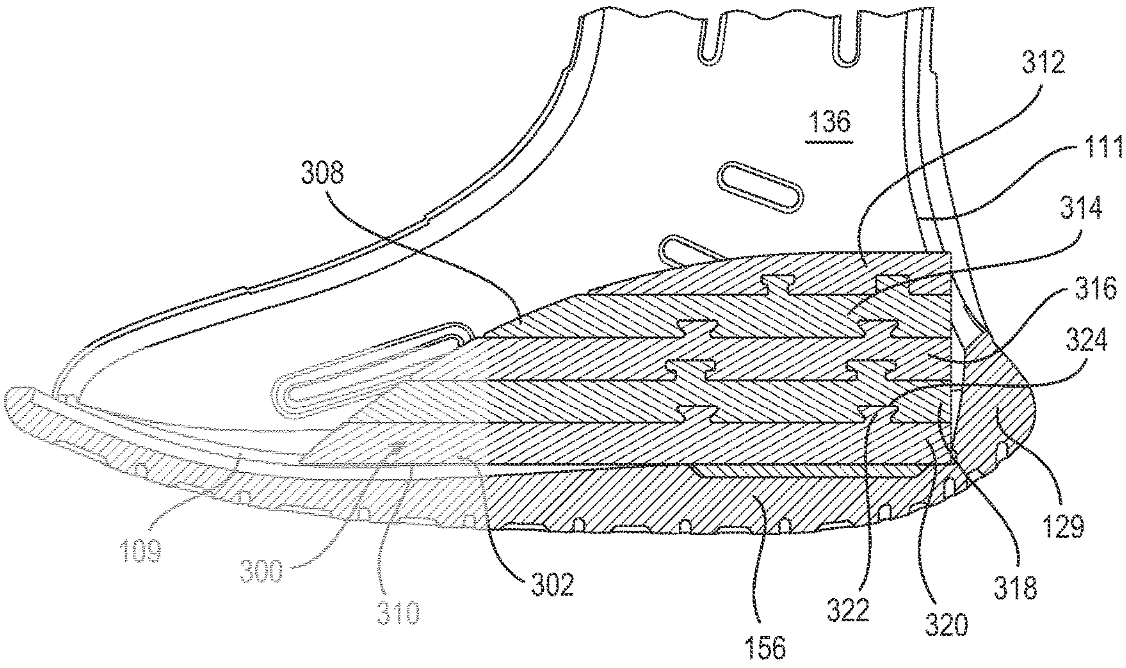
FIG. 10 is a cross-sectional view as a variation of FIG. 9, including a heel wedge.

A tread 162 of the outsole 126 of the footbed 106 may be configured with a pattern to prevent slippage and lead to smooth rollover during walking with the orthopedic walker donned. The tread 162 may be formed from the footbed 106 to limit heel and midsole height, and therefore the body 101. If a more aggressive outsole 126 may be necessary, a supplementary tread may be applied to the outsole 126 to enhance slip protection. As shown in FIG. 10, wedges may be inserted into the orthopedic walker 100 and applied along an insole to provide Achilles' tendon support and/or protection.

Figure 2:
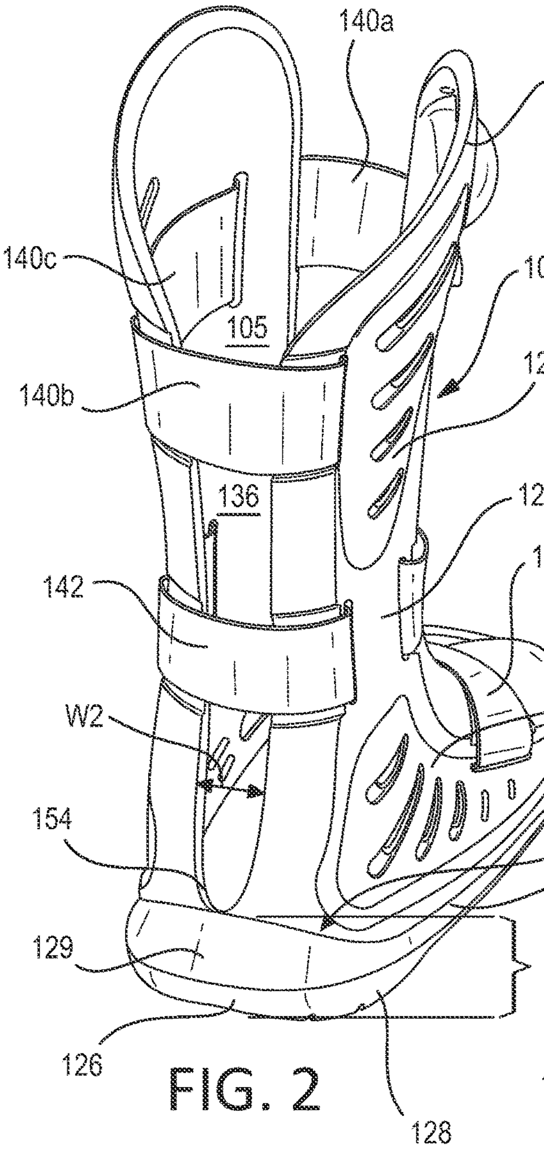
FIG. 2 is a rear perspective view of the orthopedic walker of FIG. 1.
Figure 3:
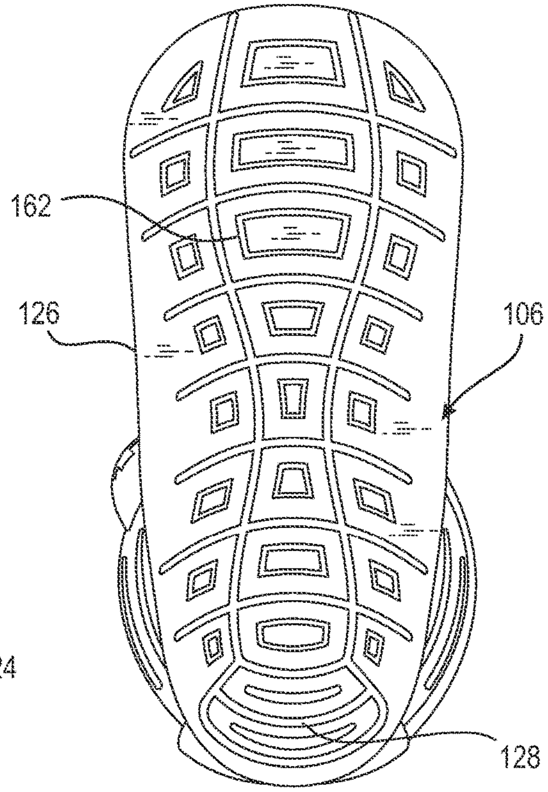
FIG. 3 is a bottom plan view of the orthopedic walker of FIG. 1.

According to the illustrated embodiment of FIGS. 1 and 2, the body 101 defines at least one anterior or posterior opening 134, 136 to facilitate donning and doffing of the orthopedic walker 100. The at least one anterior or posterior opening 134, 136 is shown in FIG. 1 as an elongated anterior opening 134, extending from a proximal portion at the end of the body 101 to a distal portion at a second end of the body 101 at the anterior side A and generally along the median plane Mp of the orthopedic walker 100. FIG. 2 shows a posterior opening 136 as an elongate opening, extending from a proximal portion at the end of the body 101 to a distal portion at a second end of the body 101 at the posterior side P likewise generally along the median plane Mp of the orthopedic walker 100. The opposed anterior and posterior openings 134, 136 allow the first and second portions 102, 104 to generally articulate relative to the median plane Mp and along the frontal plane Fp in directions A1, A2 to place the orthopedic walker 100 in an open configuration for donning the orthopedic walker.

The orthopedic walker 100 defines a proximal opening 115 between the first and second portions 102, 104, enabling a limb such as a foot to be slipped into the interior volume 105 like a boot. The anterior and posterior openings 134, 136 separate the first and second portions 102, 104, which join to seal or enclose the lower leg and foot of the user. Variable widths W1, W2 exist between at least the first and second portions 102, 104, either in the predetermined closed configuration or according to the regulation of the straps 140, 142, 144 spanning the anterior and posterior openings 134, 136. The anterior opening 134 preferably extends entirely from the toe portion 108 to the proximal opening 111, thereby forming a continuous opening on the anterior side A of the walker 100, fully separating the first and second edges 117, 118 of the body on the anterior side A. The posterior opening 136 may have a maximum width W2 at the proximal opening 115 and a taper resulting in a terminus 154 in width as the posterior opening 136 diminishes toward and terminates at the footbed 106.

Both the anterior and posterior openings 134, 136 preferably remain both before and after donning. While their widths, aside from their predetermined variability as measured from proximal and distal locations to the axis Pr–Di, and generally along with the median plane Mp along the anterior side A at least for the anterior opening 134, may fluctuate depending on the size of a user's leg, the variability in the width of the anterior and posterior openings 134, 136 are generally sized and configured to track general anatomical shapes of a human lower leg, ankle, and foot. The liner 107 may be configured to wrap about a user's lower leg, ankle, and foot and thereby offer protection to the user's leg at least within the space between the anterior and posterior openings 134, 136.

The first and second portions 102, 104 may yield to the size of the user's lower leg, ankle, and foot, thereby urging the first and second portions 102, 104 to slightly deflect relative to the median plane Mp in outward directions A1, A2, or draw closer to one another by retracting in directions opposite to the outward directions A1, A2 should the user's lower leg, ankle and foot be smaller than the predetermined open configuration because of tensioning the straps 140, 142, 144. But despite such small movement for relative sizing of a user, the material of the body 101 is sufficiently rigid to resist movement of the first and second portions 102, 104 relative to one another once the orthopedic walker 100 is donned on a user and the straps 140, 142, 144 are appropriately tensioned. The ability to flex or adjust to the size of the user's lower leg, ankle and foot, greatly enhances the orthopedic walker's 100 ability to right-size to an individual user, providing a more comfortable walker without creating pressure points due to poor sizing and chafing, and offering a more streamlined and tight-fitting orthopedic walker, particularly while walking.

Because the orthopedic walker 100 is formed from a unitary construction, the body 101 can be molded with features normally offered in a two-piece or multiple-piece walker constructions. For example, the proximal edge 116 surrounding the proximal opening 115 may be provided with a flexible, thinned edge relative to the thickness of the first and second portions 102, 104. The flexible proximal edge 116 may taper to its extreme termination, reducing chaffing and offering a smoother donning by eliminating a stiff proximal edge. The flexible proximal edge 116 may comprise a thickness variation of the first and second portions 102, 104, and offer a more intimate fit to the user by eliminating pressure points to the user at the interface where the proximal end of the first and second portions 102, 104 terminate.

Figure 4:
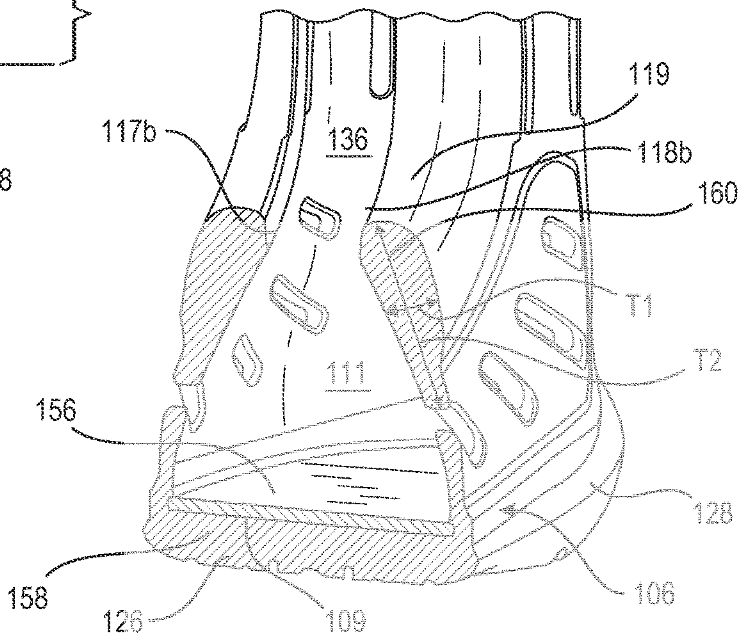
FIG. 4 is a cross-sectional view taken along line Iv-Iv in FIG. 1.

FIG. 4 provides another example of thickness variability of edges of the first and second portions 102, 104. The first portion 102 preferably defines an anterior arch 119 at the interface between the first and second portions 102, 104, and the footbed 106 on the anterior side A of the body 101. The anterior arch 119 extends over the footbed 106 and has a thickness 160 along the first edge 117, tapering in a first thickness aspect T1 distally toward the footbed 106. The anterior arch 119 is symmetrical across both the first and second portions 102, 104, and first and second sides of the footbed 106, but for exemplary purposes is described along the first edge 117.

As shown, a wall thickness along the first edge 117 may be greatest along the anterior arch 119. The anterior arch 119 may have increased material anteriorly for immobilization of the ankle as the first edge transitions between the first and second portions 102, 104 to the footbed 106. The anterior arch 119 may have a greater thickness than at adjacent areas of the first and second portions 102, 104 or first and second sides of the footbed 106. Like a traditional boot, the anterior arch 119 may form a generally inverted arcuate portion of the body 101 along the anterior side A relative to the ground. The anterior arch 119 reinforces sagittal plane immobilization.

FIG. 4 illustrates an example of how the thickness at the anterior arch 119 may be irregular or configured to optimize immobilization and cushioning along the dorsal aspect of a user's ankle and foot. The first edge 117 may have a variable thickness in at least first and second thickness aspects T1, T2, and length. The second thickness aspect T2 may taper relative to the extent the first edge 117 extends over the dorsal aspect of the user's ankle or foot. The first thickness aspect T1 may taper distally as less support or cushioning is required for the medial, lateral sides of the foot. By modifying the material thickness while the body 101 is a unitary structure, the orthopedic walker 100 is advantageous. It can minimize supplemental means for stabilizing and cushioning, such as padding.

Returning to FIGS. 1 and 2, the orthopedic walker 100 includes the pump 110 secured to the body 101. The pump 110 preferably fits in an opening 114 formed by the first portion 102 of the body 101. The pump 110 may be mounted over the exterior surface 103 of the orthopedic walker, but in each variation body 101 provides a stable platform for a user to regulate the pump 110 and subsequent fitting of a liner 107 about the lower leg, ankle and foot. The pump 110 is well exposed at the proximal end of the body and enables easy manipulation of the pump to regulate air in the bladder with a valve 112 communicating with the pump 110 and liner 107. The valve 112 may also fit in an opening 113 formed by the first portion 102.

The first portion 102 defines at least first and second regions 120, 124 about at least the exterior surface 103 of the body 101. The first and second regions 120, 124 may demarcate or be distinguished from a connecting region 122 adjacent to the first and second regions 120, 124. The first region 120 may have a different color or texture from the connecting region 122.

The first region 120 may be formed from a different material and/or has different structural properties from the connecting region 122. For example, in a variation, the first region 120 may be formed from a stiffer material or be rendered stiffer than the connecting region 122 to offer greater support and stabilization. In another variation, the first region 120 may be treated differently than the connecting region 122 for enhanced stabilization. In yet another variation, the first region 120 may include additives to enhance the stiffness relative to the connecting region. However, in each variation, the first and connecting regions 120, 122 are arranged integrally and bonded chemically within interchanging or blending portions of their material to form a continuous structure.

The connecting region 122 may surround each of the first and second regions 120, 124. The orthopedic walker 100 is not limited to first and second regions 120, 124 but may include many regions to serve a stated purpose. Even the connecting region 122 may abut other regions forming peripheral edges of the body 101, with the connecting region 122 and the other of such regions differing by at least one feature including color, texture, stiffness or rigidity, and structural features such as thickness and openings.

The body 101 may include strategic features according to the desired properties of the orthopedic walker 100. For example, the first and second regions 120, 124 define at least one ventilation opening 150, 151 extending through a thickness of the first portion 102. The at least one ventilation opening 150, 151 may include, as shown, at least two ventilation openings arranged in a shape corresponding to a shape of the first region 120 for aesthetic, structural (such as improved flexibility), or desired ventilation purposes.

FIGS. 1, 2, and 4 illustrate the footbed 106 as defining an outsole 126 continuously formed from a material forming the footbed 106 inclusive of an insole 109 of the footbed 106. The outsole 126 may have a molded structure forming part of the footbed 106 instead of a separate and discrete outsole tread, negating an outsole 126 being attached to the footbed 106. A sole insert 156 may be within the footbed 106 and along the interior surface 111 of the insole 109 to provide additional support and cushion for the foot of the user.

Regulating and minimizing the height is an objective of the design of the orthopedic walker 100. The footbed 106 defines a heel roll region 128 at a posterior end of the footbed 106. The heel roll region 128 preferably includes a heel extension 129 protruding posteriorly P from the terminus 154 at the junction of the footbed 106 and relative to and from the first and second portions 102, 104 and extends the outsole 126 and heel roll region 128. The heel extension 129 is adapted to assist with shock absorption at the heel region of the footbed at heel strike by the user.

The footbed 106 may define a maximum stack height 152 of a heel lift 158 relative to the toe region 108, with the insole 109 increasing in height relative to the outsole 126 posteriorly. To keep the height of the orthopedic walker 100 at a minimum, a maximum stack height 152 is in the range of 20 mm to 30 mm, and more preferably 25 mm.

Figure 5A:
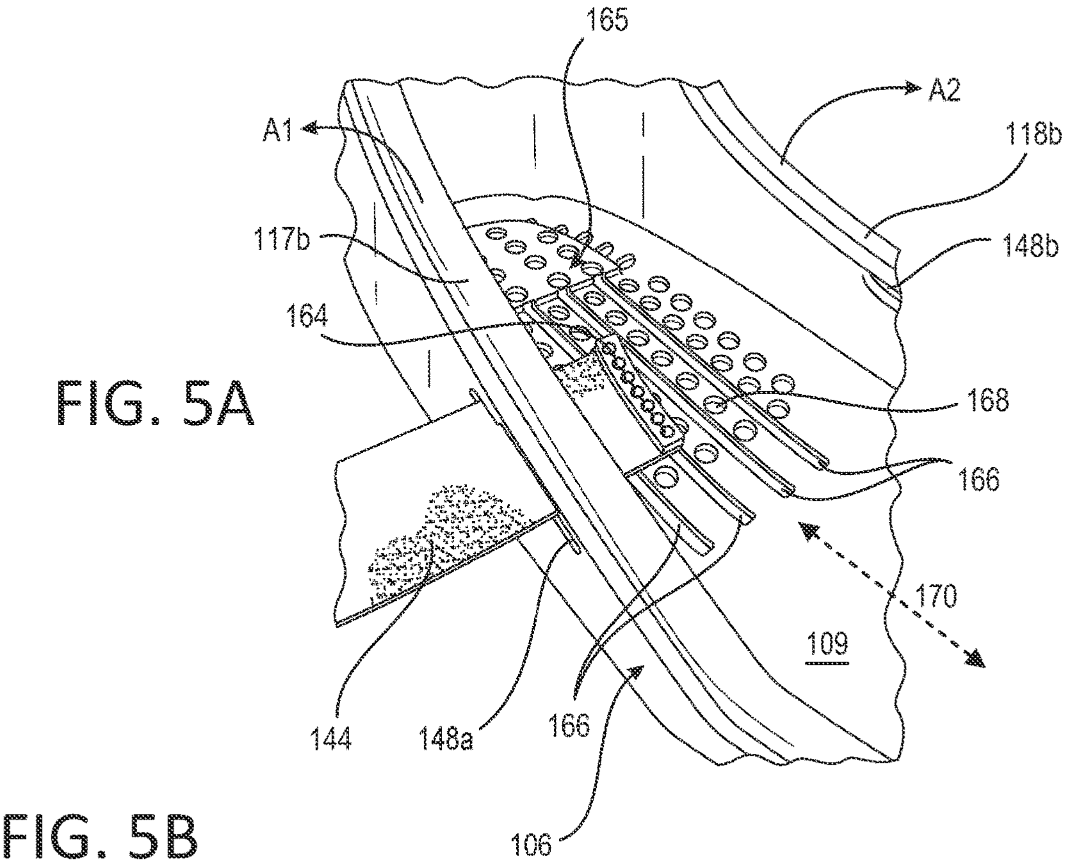
FIG. 5A is a perspective sectional view of a variation of an insole of the orthopedic walker in FIG. 1.
Figure 6:
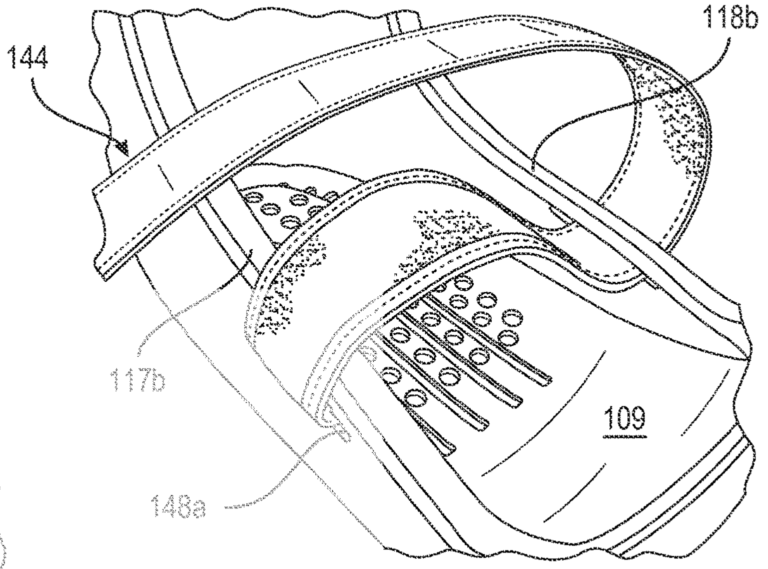
FIG. 6 is a perspective sectional view of a strap variation in the orthopedic walker of FIG. 1.

Referring to FIGS. 2, 5A, and 6, the straps 140, 142, 144, with strap 144 serving as the example, extend over at least part of the exterior surface 103 and along the interior surface 111, and across at least one of the anterior and posterior openings 134, 136. Each of the straps 140, 142, 144 is preferably secured to the body 101 without adhesives. For example, the strap 144 includes a retainer 164 secured to a first end thereof. The retainer 164 is preferably dimensioned and configured larger than the opening 148 to be retained against one of the exterior surface 103 or interior surface 111. This arrangement is advantageous because the strap 144 may be removed from the orthopedic walker 100 instead of being secured to the body 101 by a fastener or adhesive and can be trimmed to the size of a user.

The strap 144 is arranged to extend along the interior surface and exterior surface 111, 103 of the body 101 while spanning the anterior and posterior openings 134, 136, thereby forming a circumferential strap system about the orthopedic walker 100. The circumferential arrangement of the combined circumference of the strap 144 and the body 101 enables the orthopedic walker 100 to be stably secured to the user without creating a tourniquet effect if the strap 144 itself fully encircled the lower leg. The circumferential arrangement also enables slight adjustment of the anterior and posterior openings 134, 136 according to the size of a user's lower leg, ankle, and foot, but with the body 101 being sufficiently rigid to resist movement of the lower leg, ankle and foot once the straps 140, 142, 144 are properly tensioned on the user.

To maintain the streamlined profile, the exterior surface 103 forms at least one indent 146 configured and dimensioned to a width of the at least one strap 140, 142, 144 in which the at least one strap 140, 142, 144 is retained. Due to the unitary form construction of the body 101, the at least one indent 146 can be molded into the body 101, and mitigate the strap from catching onto objects when the orthopedic walker 100 is worn, such that the at least one indent 146 can track the position of the strap 140, 142, 144 about the exterior surface 103 or at least be position adjacent an opening to suppress the extent the strap peers over the exterior surface 103 of the body 101. The interior surface 111 may also form indents corresponding to the strap to minimize pressure points within the orthopedic walker 100 and retain the strap in a fixed location.

Figure 5B:
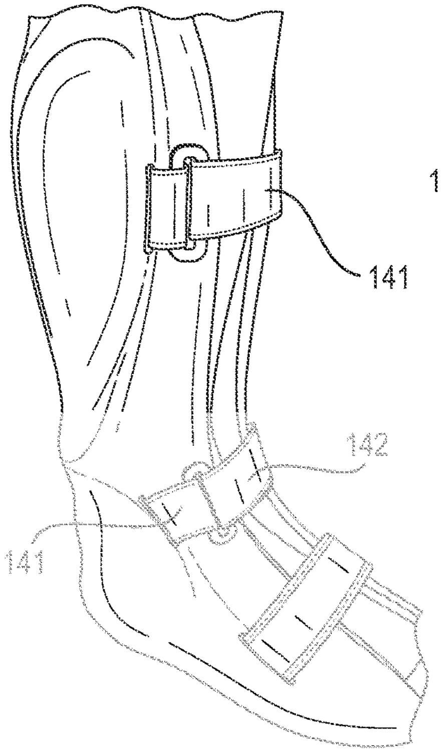
FIG. 5B is a perspective view of a variation of the strap arrangement.

In a variation or combination with the retainer 164 in FIG. 5B, the first and second straps 140, 142 may be secured to D-rings 141 carried by the first end of the corresponding strap. As the first and second straps 140, 142 weave in and out of the body 101 along with the interior and exterior surfaces 111, 103 of the body 101, the D-ring 141 acts as a stop when the first and second portions 102, 104 are opened for donning and doffing. The straps 140, 142, 144 slide through the body 101 when the first and second portions 102, 104 are placed in the open configuration.

The arrangement of the straps as sliding and weaving along the exterior and interior surfaces 103, 111, as depicted, and extending through the corresponding openings allows the straps 140, 142, 144 to stay fixed to the first and second portions 102, 104 when the orthopedic walker 100 is in the open configuration. A variation includes how the liner 107 retains the straps, so the liner 107 remains attached to the body 101 when the orthopedic walker 100 is in the open configuration.

FIGS. 5A and 6 show the first and second portions 102, 104 as forming the opposed openings 148 through which the strap 144 extends from the interior surface 111 to the exterior surface 103. The strap 144 has a first segment adapted to loop over at least one of the first and second edges 117, 118 of the first and second portions 102, 104, respectively, and return to another one of the first and second portions 102, 104, or overlap a second segment of the strap.

FIG. 5A depicts the insole 109 defining at least one channel 166 disposed along the midline 170 of the footbed 106. The at least one channel 166 facilitates articulation of the first part 102 relative to the second part 104 in the first and second directions A1, A2 for enlarging the anterior and posterior openings 134, 136. The insole 109 also defines at least one aperture 168, located between at least two channels 166 for improving articulation of the first and second portions 102, 104 relative to one another in the first and second directions A1, A2. At least one aperture 168 provides cushioning during heel strike and attributes to reducing the height of an insole 109, thereby keeping the walker's heel height at a minimum.

As an alternative, referring to the embodiment of FIG. 5A combined with the embodiment of the orthopedic walker 380 of FIGS. 13-16, the at least one channel 166 may be provided to prevent squeaking between the bottom of the body 381 and the frame insert 383 and prevent shifting during gait. The at least one aperture 168 may be provided for the heel 165 of the insole 109 to extend through the frame insert 383 during heel strike to reduce the height of the insole 109 necessary and overall heel height of the orthopedic walker 380.

Figure 7:
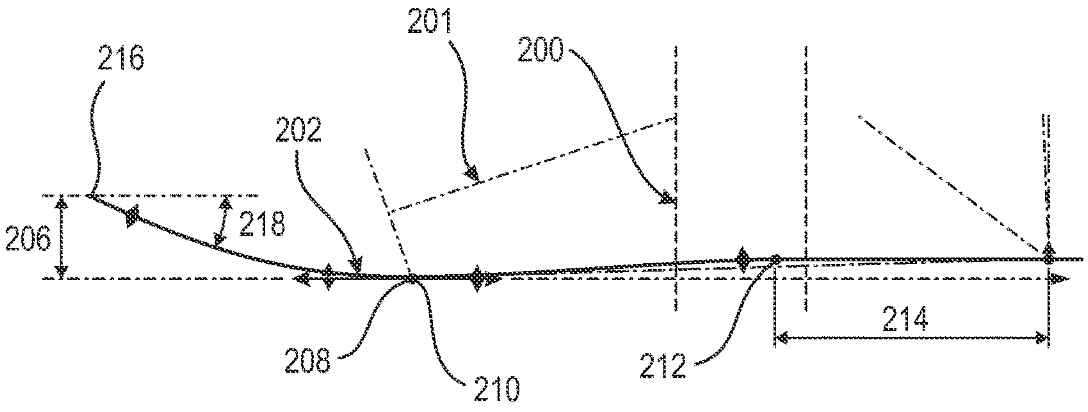
FIG. 7 is a schematic view exemplifying the dimensions and contour of an insole in the orthopedic walker of FIG. 1.
Figure 8:
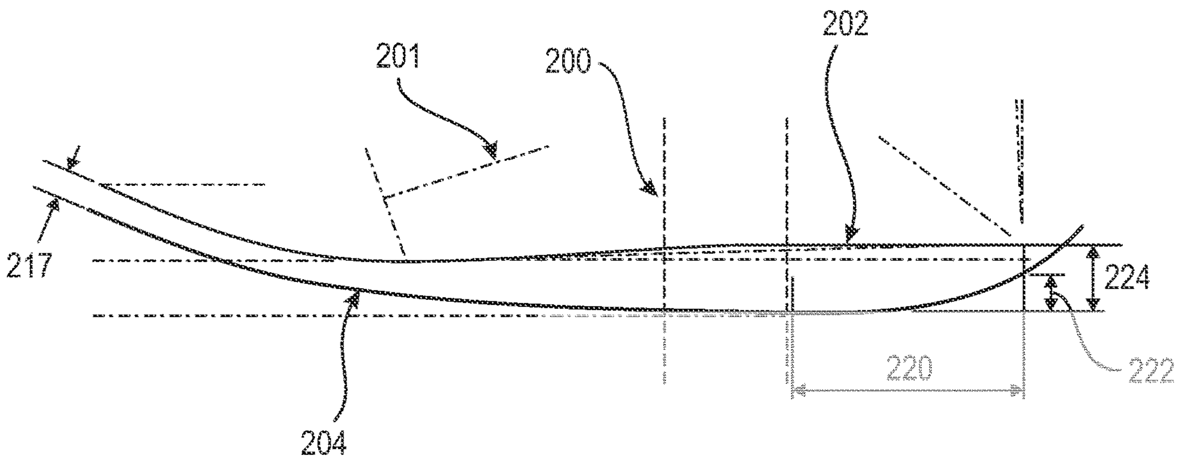
FIG. 8 is a schematic view exemplifying the dimensions and contour of an outsole in the orthopedic walker of FIG. 1.

FIGS. 7 and 8 exemplify how the footbed aspect 201 of the orthopedic walker 100 is based on a traditional shoemaker's template. A common complaint of conventional walkers is that the calf or corresponding lower leg portion does not fit well, with the corresponding calf portion being too far displaced anteriorly. Another issue with current walkers is that the apex of the rocker is not biomechanically neutral when standing. The rocker sole of current walkers will roll too far forward or too far back when standing, therefore causing an imbalance. In the orthopedic walker of the embodiments herein, the contours of the insole contour 202 and outsole contour 204 are arranged with respective dimensional relationships and corresponding dimensions to remedy the shortcomings of known orthopedic walkers.

According to FIG. 7, a calf aspect 200 of the body 101, as referenced in preceding embodiments, is placed more posteriorly according to the relative extension from a footbed aspect 201. The calf aspect 200 intersects an apex of the outsole contour 204, such that a rocker configuration of the outsole contour 204 is neutral at standing.

A maximum heel height 224 from the apex to a heel plate 214 of the insole contour 202 is 18 to 32 mm, and more preferably 20-26 mm. The heel plate 214 preferably extends substantially parallel to the apex or ground.

According to preferred dimensions, as depicted in FIGS. 7 and 8, the dimensions of an exemplary insole contour 202 as follows with a 5-10% tolerance depending on the side of the footbed aspect 201; however, the dimensional ratios are substantially the same: toe raise 206 is 23 mm, MT spline length 1 208 is 100 mm, the MT spline length 2 210 is 130 mm, the heel spline length 212 is 60 mm, the length of the heel plate 214 is 79.6 mm, the toe distance 216 is 70 mm and the angle 218 is 23 degrees. For the outsole, the preferred dimensions are, taking the same tolerance and qualification for the outsole contour 204 are: toe thickness 217 8 mm, apex line length 220 is 60-80 mm, the heel raise 222 is 11 mm, and the heel height 224 is 20 mm. The dimensions are subject to change, but the overall intentions of the dimensions are stated above in creating a more posteriorly direction calf support, more neutral apex, and a reduced heel height.

Figure 9:
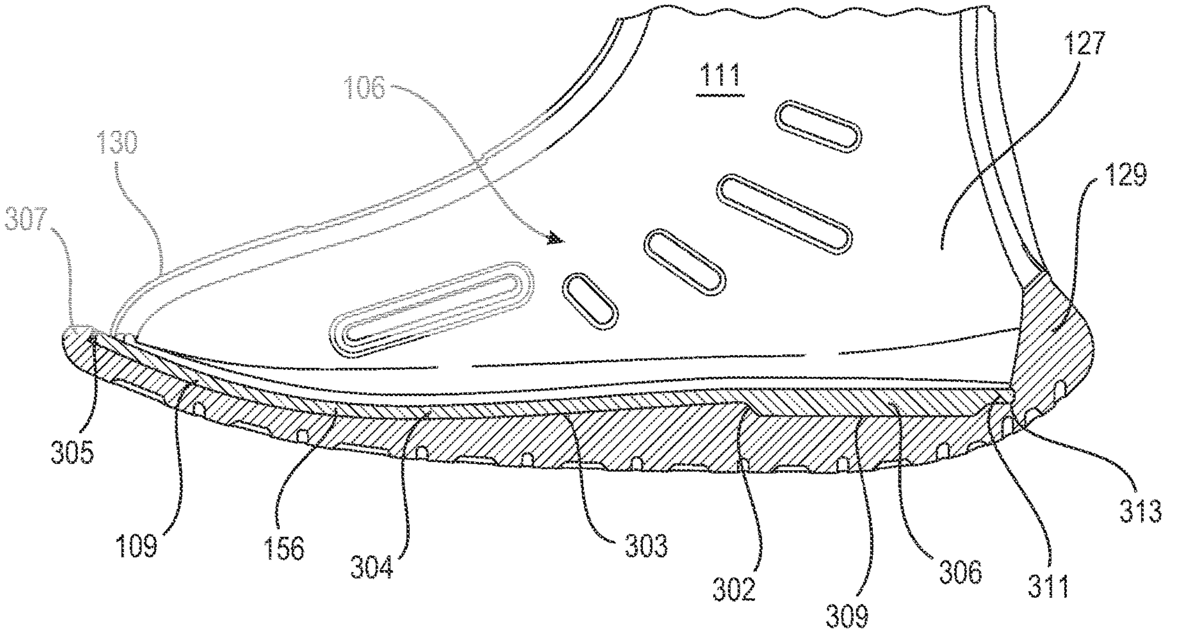
FIG. 9 is a cross-sectional view taken along line IX-IX in FIG. 1.

FIG. 9 illustrates the interior surface 111 of the footbed 106 as defining an insole recess 302 located along an insole surface 303 configured and dimensioned to receive a sole insert 156. The insole recess 302 may define a toe recess 305 at the toe region 130 configured and dimensioned to a thickness of the sole insert 156, so the sole insert 156 does not preferably protrude above a height 307 of the insole surface 303, as defined at the toe region 130. The insole recess 302 may define a heel recess 309 extending distally into the footbed 106 more than the toe recess 305. The insert 304 has a heel portion 306, defining a greater thickness at the heel recess 309.

The insole recess 302 may define a recess 313 extending into the heel extension 129, and the sole insert 156 defines a posterior flange 311 extending into the recess 313. The recess 313 extends circumferentially about the heel portion 127, where the insole insert 156 sits inside the footbed to retain the insole insert 156 with the toe recess 305 with no gluing the insole insert 156 adding unwanted heel height. The insole recess 302 is preferably arranged so the insole insert 156 is a softer material than the material forming the footbed 106, such that with the increased insole insert thickness at the heel portion 306, the heel height can be reduced, which is a problem among orthopedic walkers, offering a lower heel height to match the unaffected foot and leg of a user.

FIG. 10 shows a heel wedge 300 adapted to fit within the interior volume 105 and contour to the interior surface 111 and the insole 109. The heel wedge 300 includes at least two layers 312, 314, 316, 318, 320 stacked over one another to increase heel height with the sole insert 156. The heel wedge 300 includes interlocking features 322, 324 among the at least two layers 312, 314, 316, 318, 320 to lock the at least two layers relative to one another. The heel wedge 300 has a proximal contour 308 different from a distal contour 310.

Figure 10A:
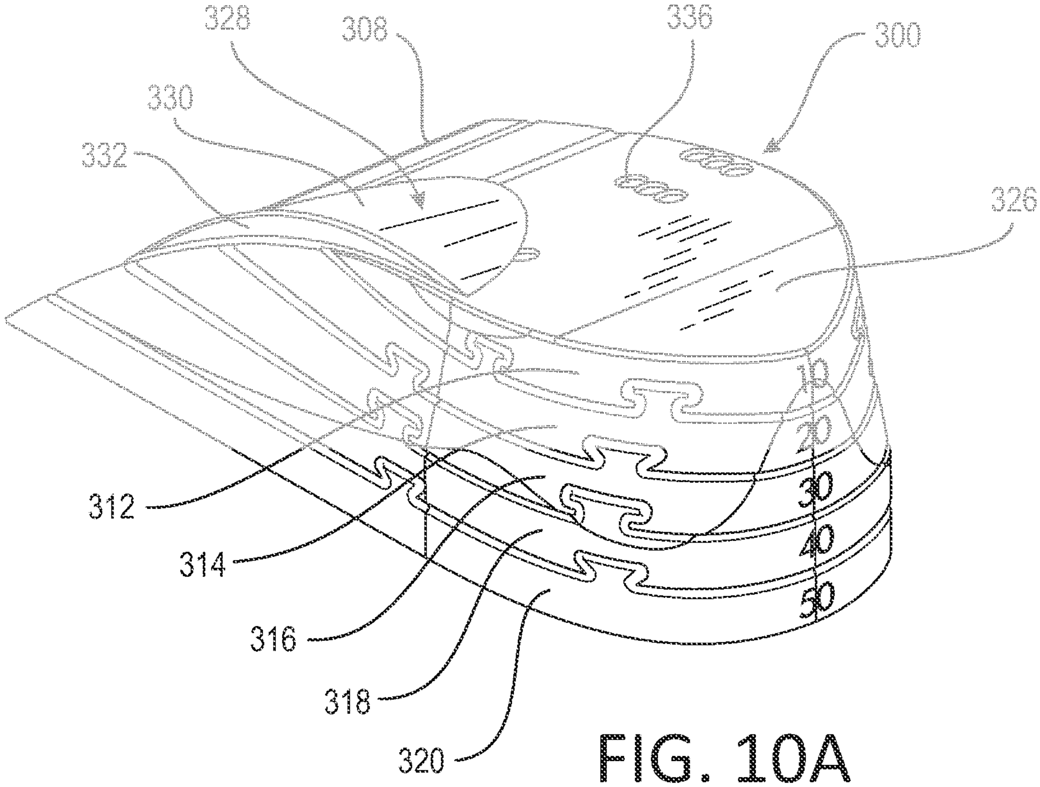
FIG. 10A is a perspective view of the heel wedge of FIG. 10.
Figure 10B:
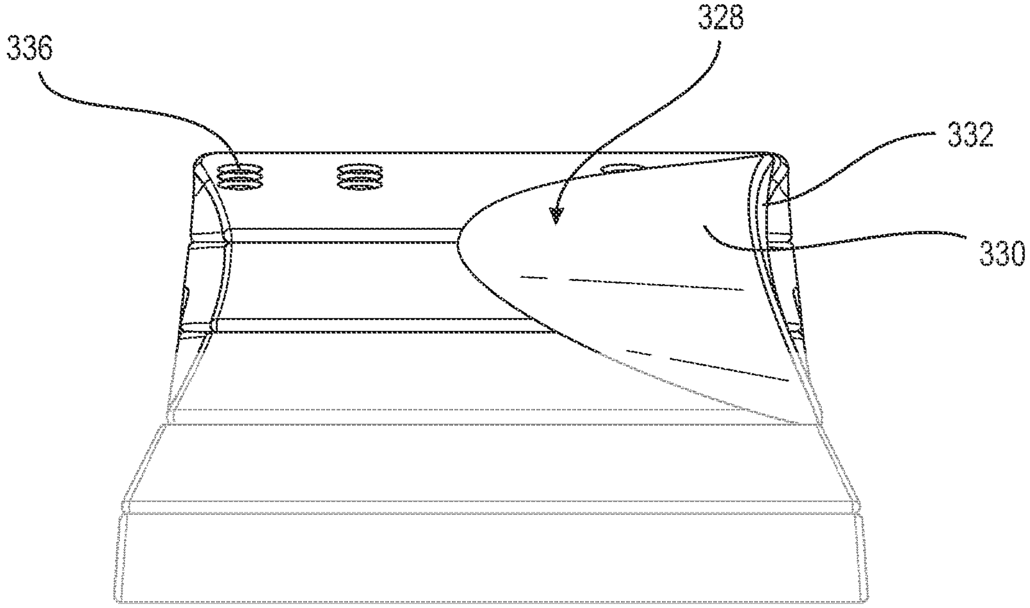
FIG. 10B is a frontal perspective view of the heel wedge of FIG. 10A.

FIGS. 10A and 10B exemplify the heel wedge 300 in greater detail. The heel wedge 300 may include indicia 326 anywhere on at least two layers 312, 314, 316, 318, 320, to indicate the angle or relative height provided by the heel wedge 300. For example, the indicate 326 is represented on the posterior of each of the at least two layers 312, 314, 316, 318, 320, indicating the angle produced by the stacking of the at least two layers 312, 314, 316, 318, 320.

The heel wedge 300 according to the interior contours of the inner volume 105 of the body 101 of the orthopedic walker 100. The first layer 312 defines a top surface upon which a heel of a user is placed. A heel arch 330 may be placed along the top surface (generically representing the top surface of at least two layers) and may likewise extend along anterior portions of other layers, as depicted in FIG. 10B. As the heel wedge 300, or the composite of the at least two layers 312, 314, 316, 318, 320, is contoured to fit within the inner volume 105, the heel wedge 300 may be provided with lateral or medial contours 332, 334 to snugly fit to the specific interior contours of the inner volume 105. Likewise, to minimize heat generated by heel friction to the top surface, the at least two layers 312, 314, 316, 318, 320 may be provided by perforations 336 extending through, partially or entirely, a thickness of each of the at least two layers or a single layer.

By contouring the heel wedge 300 according to the inner contours of the inner volume 105, the heel wedge 300, either as a composite of the at least two layers 312, 314, 316, 318, 320 or a single one of such layers, the heel wedge 300 is maintained in place in the inner volume 105 without the need for attachment provisions.

Figure 11A:
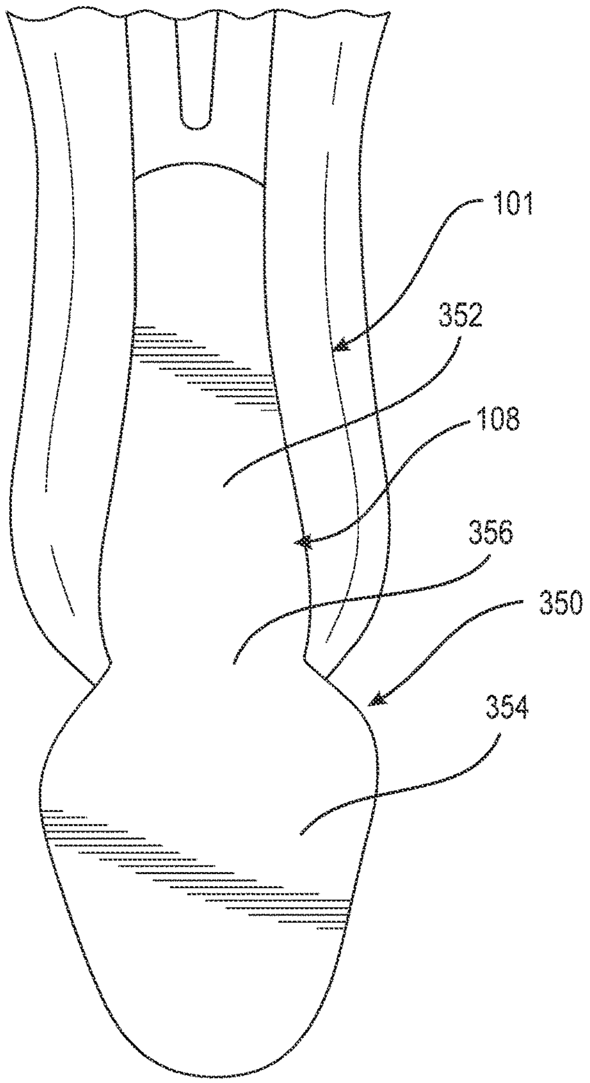
FIG. 11A is a first exemplary view of a variation of an orthopedic walker, including a heel insert having a toe guard.
Figure 11B:
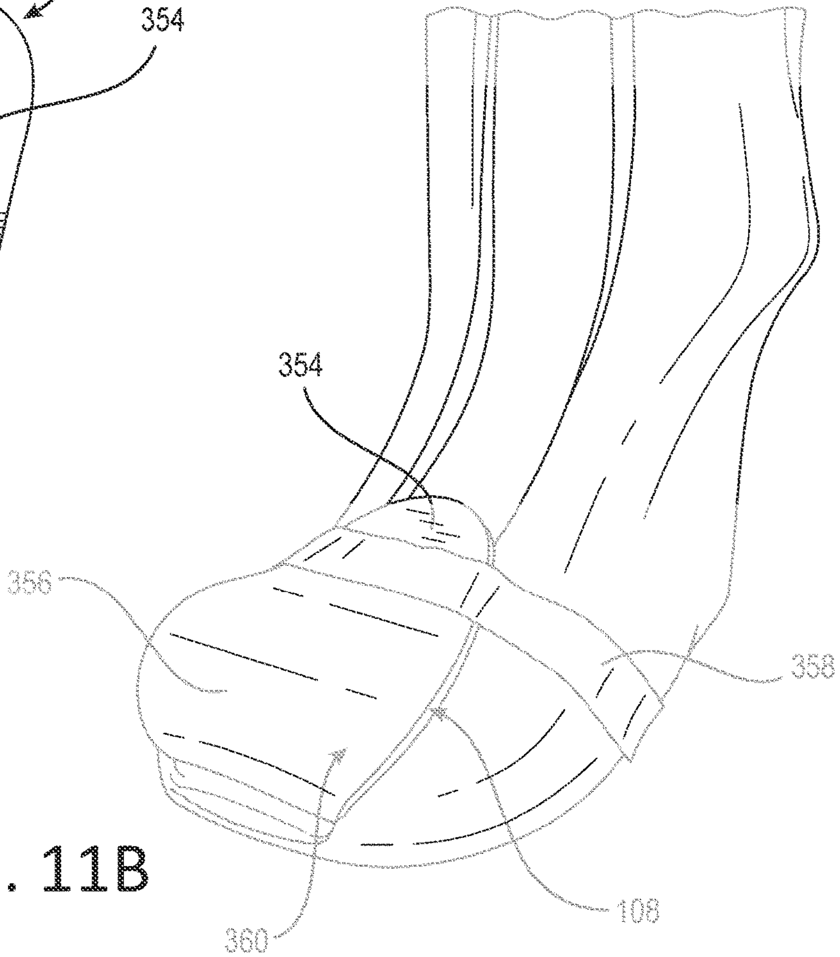
FIG. 11B is a second exemplary view of the orthopedic walker, including the toe guard closing a toe opening.

FIGS. 11A and 11B illustrate an insole insert 350, having an insole portion 352 and a toe guard portion 354. The toe guard portion 354 is configured and dimensioned to extend beyond the open toe region 108 and fold at a bend portion 356 connecting the insole portion 352 and the toe guard portion 354 so the toe guard portion 354 spans the open toe region 108. The toe guard portion 354 preferably is maintained in place spanning the open toe region 108 by a fastener 358, or wedged against the orthopedic walker body 101 to stay secure.

Figure 12A:
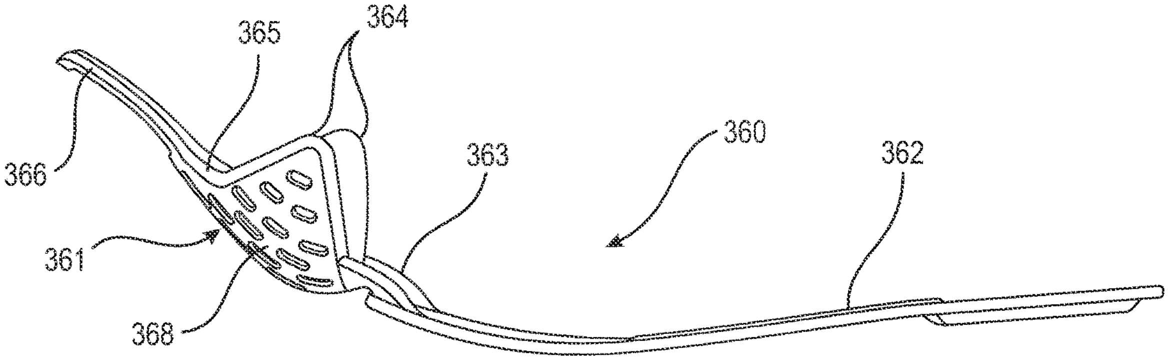
FIG. 12A is a perspective view of another embodiment of a toe guard.
Figure 12B:
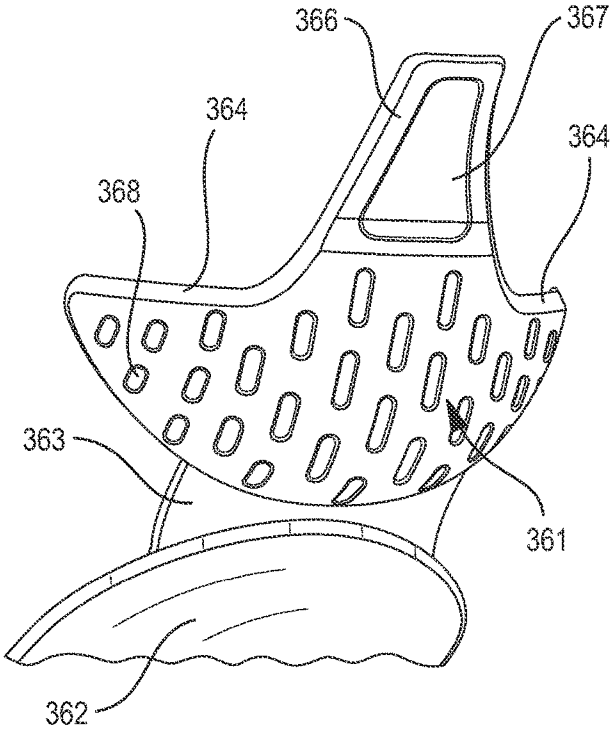
FIG. 12B is a sectional view of the toe guard of FIG. 12A.
Figure 12C:
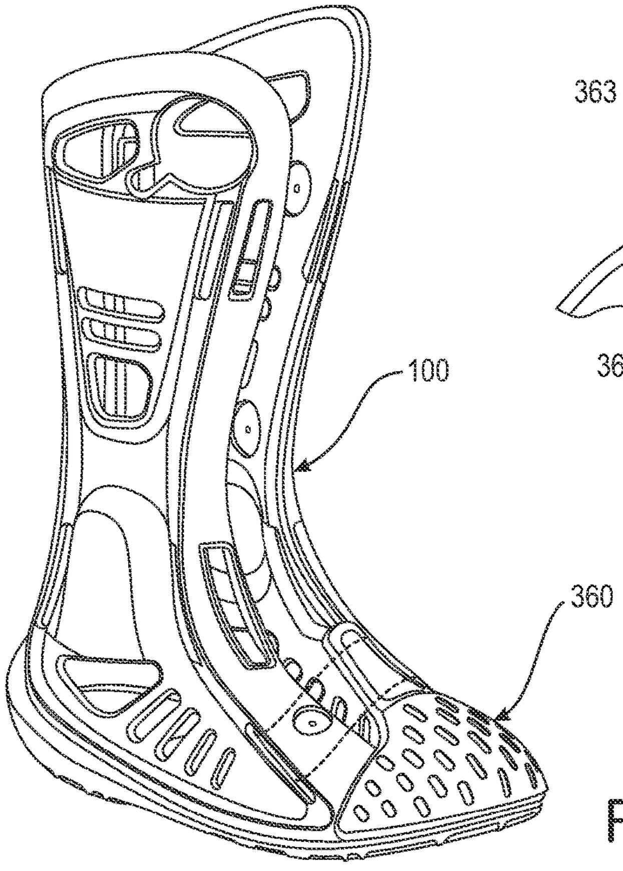
FIG. 12C is a perspective view of an orthopedic walker having the toe guard of FIG. 12A.

FIGS. 12A-12C exemplify a variation of a toe guard 360 useable with the orthopedic walker embodiments 100 described herein. FIG. 12A depicts the toe guard 360 as having a toe cup or portion 361 adapted to cover the user's toes. The toe guard 360 has a unitary structure. It continuously and interruptedly consists of a monolithic structure with the toe portion 361, an insole portion 362, and a connecting portion 363 flexibly linking the toe portion 361 to the insole portion 362. When inserted into the inner volume 105 of the body 101 of the orthopedic walker 100, a clinician need place only the insole portion 362 into the footbed 106 of the body 101. The toe portion 361 extends from the connecting portion 363 so it is automatically placed in the open toe region 108.

If it is not desired to include the toe portion 361, a clinician may sever the connecting portion 363 from the insole portion 362, thereby the toe portion 361 remaining with the severed connecting portion 363. Otherwise, if the toe portion is needed, the clinician may fit the toe portion 361 within the open toe region 108, with wing portions 364 tailored to abut along its edges 365 or rest against the body 101, protecting the user's toes. The toe portion 361 may include a tongue 366 extending from an end opposite the connecting portion 363, and may include fastener material 367 (such as hook and loop) engageable with a toe strap, thus preventing the toe portion 361 from reverting to the open configuration. The toe portion 361 may be perforated with perforations 368 to improve breathability.

The toe guard 360 is preferably molded in an open configuration, as illustrated in FIG. 12A, to reduce tool complexity for making the toe guard 360, but for also placing the toe portion 361 in a predetermined configuration for initial fitting and without interfering with insertion of the insole portion 362 into the foot boot.

Figure 13:
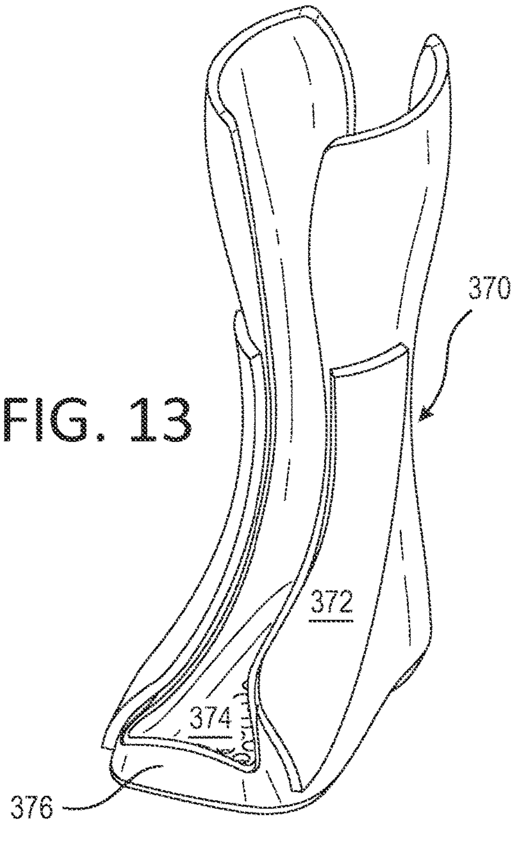
FIG. 13 is a perspective view of another embodiment of an orthopedic walker having an integrated toe guard.
Figure 14:
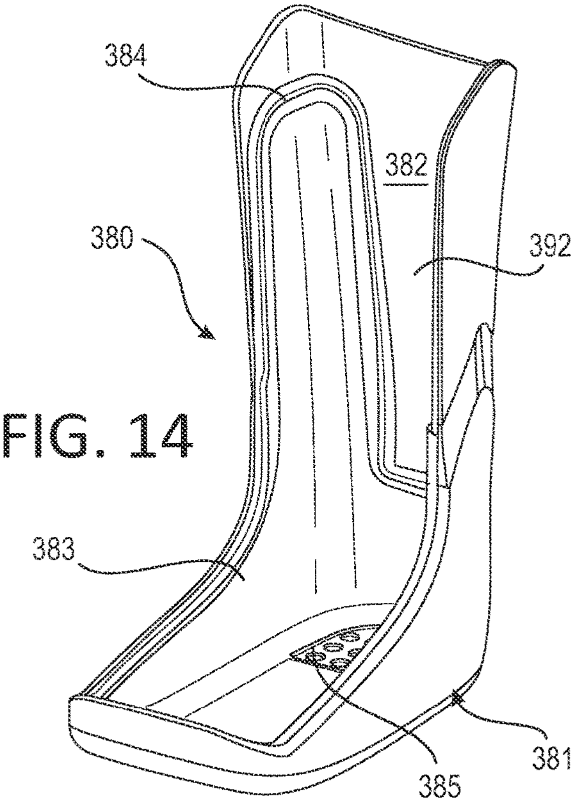
FIG. 14 is a perspective view of another embodiment of an orthopedic walker.
Figure 15:
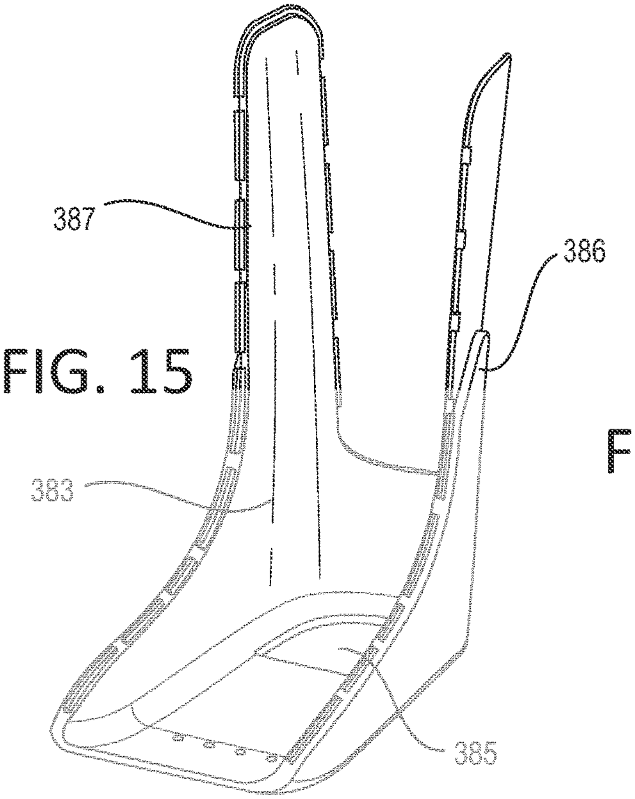
FIG. 15 is a perspective view of a frame insert in the orthopedic walker of FIG. 14.
Figure 16:
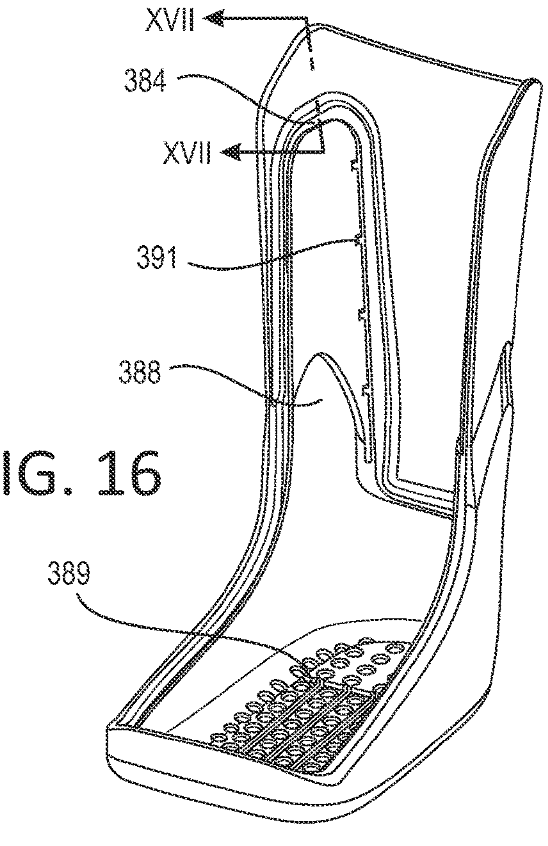
FIG. 16 is a perspective view of the walker body in the orthopedic walker of FIG. 14.
Figure 17:
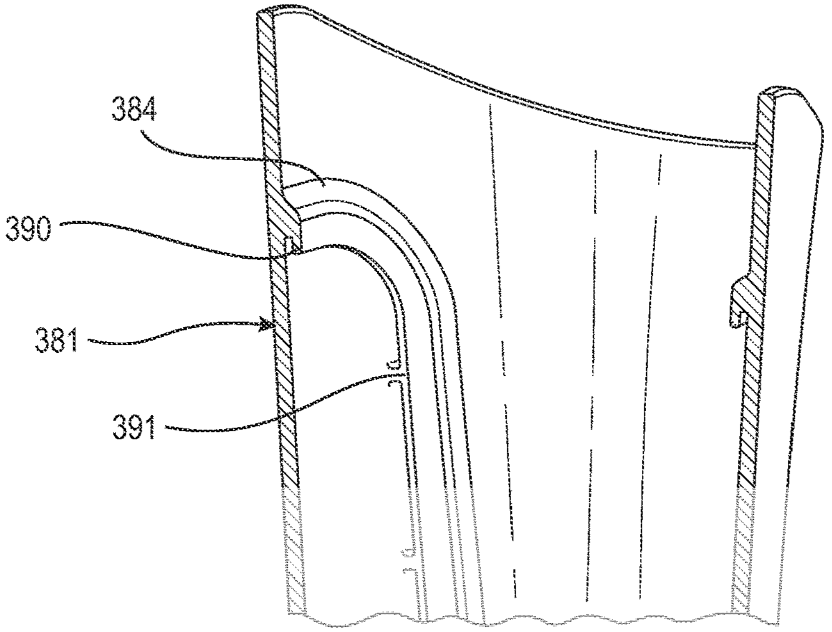
FIG. 17 is a cross-sectional view taken along line XVII-XVII in FIG. 16.

In contrast to the prior art systems, FIG. 13 illustrates an orthopedic walker 370 that may be configured with a closed-toe portion 374 with a toe guard 376, as shown in FIG. 13, that surrounds and protects but does not tightly wrap the toes of a user, resulting in increased comfort over existing walkers. The closed-toe portion 374 offers a protective barrier from the environment without adding significant bulk to the orthopedic walker body 372. The closed-toe portion 374 is preferably contoured anatomically to toes and improves gait, while the orthopedic walker 370 is worn compared to conventional walkers, making it easier for the user to walk with the orthopedic walker 370 donned.

FIGS. 14-17 illustrate another embodiment of an orthopedic walker 380 having a body 381 formed in a unitary construction and a frame insert 383 adapted to line an interior volume 382 of the body 381. The frame insert 383 is preferably formed from a stiffer material than the body 381. The frame insert 383 includes a raised portion 386 configured and dimensioned to fit within a recess 388 defined by the body 381 to interlock the frame insert 383 to the body 381. The frame insert 383 may define at least one opening 385 arranged to correspond to a region 389 of the body 381.

The frame insert 383 may define a plurality of tabs 387 extending along a periphery and arranged to insert within a retaining rib 384 defined by the body 381. The retaining rib 384 preferably includes a plurality of dividers 391, interlocking the periphery of the frame insert 383 between the plurality of tabs 387. The retaining rib 384 forms an undercut 390 into which the plurality of tabs 387 insert. A posterior portion 392 is preferably recessed relative to the retaining rib 384 and enables trimming thereof should the user have a larger calf.

Figure 18:
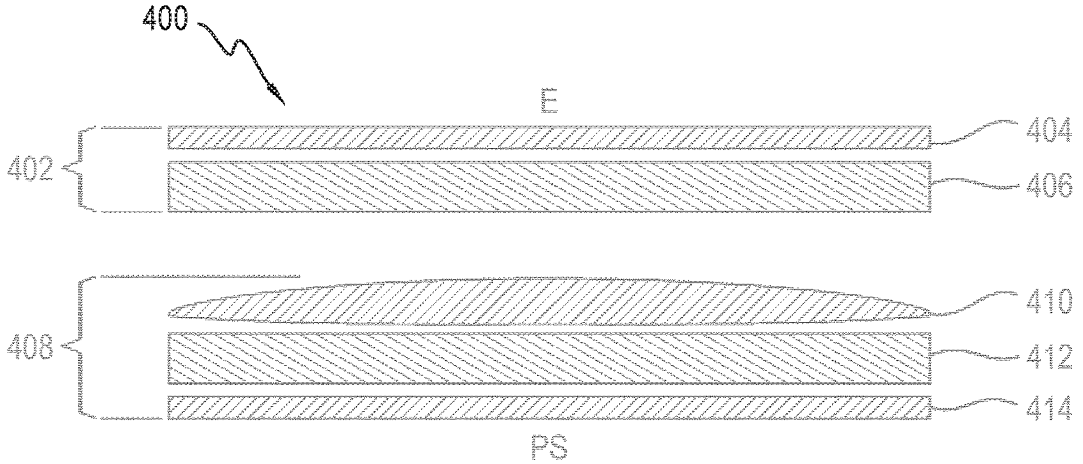
FIG. 18 is a schematic view of a cross-section of an embodiment of a liner.

FIG. 18 shows an exemplary liner 400 for an orthopedic walker, including a first laminated structure 402 has a loop material layer 404 and a foam layer 406, secured to a second laminated structure 408 including a bladder layer 410, a foam layer 412, and a loop material layer 414. The liner 400 is preferably arranged to communicate with the pump 110 and valve 112 and line the interior surface 103 of the orthopedic walker 100.

Figure 19:
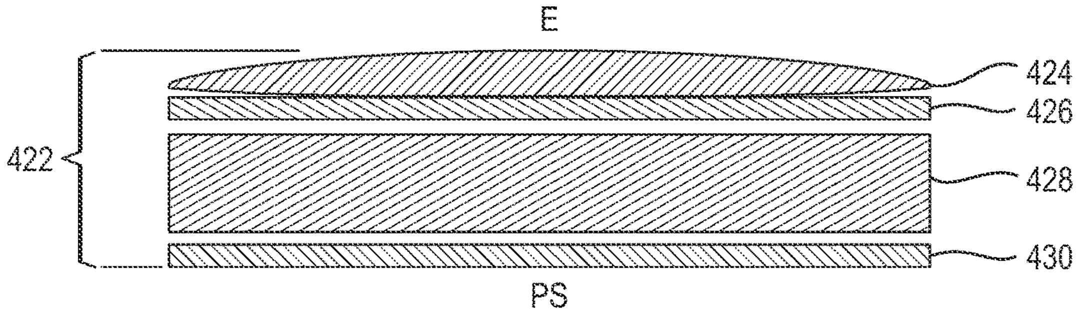
FIG. 19 is a schematic view of a cross-section of another embodiment of a liner.

FIG. 19 illustrates another embodiment of a liner 422, including a bladder layer 424 extending along a first side and surface of the liner 422, and secured to a first loop layer 426 sandwiching a foam layer 428 with a second loop layer 430 forming a second side and surface of the liner 422. The liner 422 may be die-cut, and the layers need not be stitched, and the edges may be heat welded together.

FIGS. 20A-20D depict another embodiment of an orthopedic walker 500, according to embodiments, variations, and concepts discussed in this disclosure. As with the orthopedic walker 100, the orthopedic walker 500 includes a unitary body 501 preferably formed by a polymeric material, specifically with an EVA. The unitary body 501 defines first and second portions 502, 504, and defines exterior and interior surfaces 503, 505. A footbed 506 is formed by the unitary body 501, and the unitary body 501 has an open toe region 508, as in the preceding embodiments.

As in variations described, a toe guard 510 may be inserted in the open toe region 508, or as in the embodiment of the orthopedic walker 500, a toe guard 510 may be formed along an anterior lip of the open toe region 508. The toe guard 510 is preferably molded together and is formed by and consists of the unitary body 501. The toe guard 510 generally extends perpendicularly relative to the footbed 506, and connects the first and second portions 502, 504. The toe guard 510 may be trimmable according to the needs of a user.

As the orthopedic walker 500 is formed as a boot-like structure, replete with the desired flexibility to open and close against a user's foot and lower leg, the unitary body 501 may define handles 512 arranged to facilitate pulling the orthopedic walker 500 onto the foot and lower leg of the user. The handles 512 may be shaped in any manner ergonomically, enabling donning of the orthopedic walker 500. In the illustrated example, the handles 512 are preferably located at an upper or proximal end of the unitary body 501, sized sufficiently for fingers of the user to be inserted thereinto grasp and pull the orthopedic walker on the user's leg. However, additional handles 522 located distally relative to the proximal end should a user need to grasp the orthopedic walker at a different location to better don the orthopedic walker.

Figure 23A:
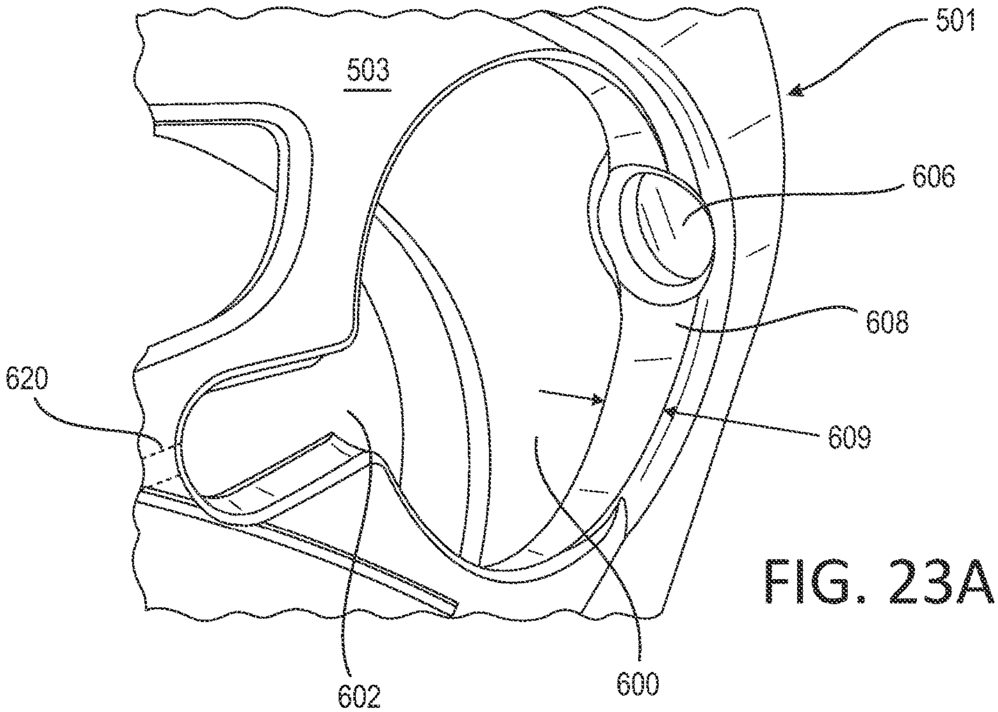
FIG. 23A is a sectional view of the orthopedic walker of FIG. 20A, showing an opening for a pump.
Figure 23B:
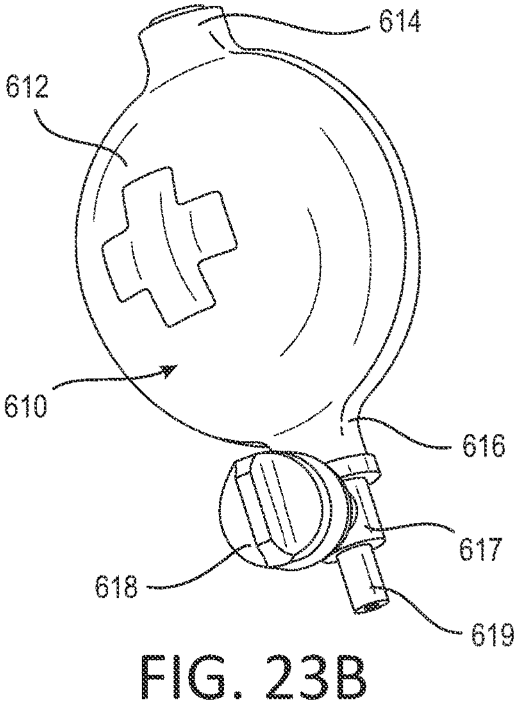
FIG. 23B is a perspective view of a pump for the orthopedic walker of FIG. 20A.
Figure 23C:
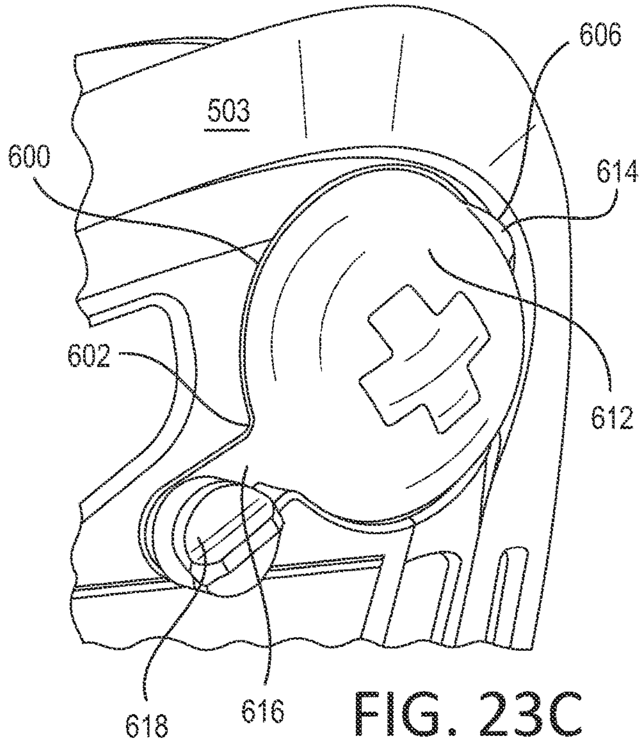
FIG. 23C is a sectional view showing the pump of FIG. 23B in the opening of FIG. 23A.

The unitary body 501 defines an opening for inserting and removing a pump assembly for an inflatable softgood assembly, discussed more fully in connection with FIGS. 23A-23C. As the unitary body 501 is unitary, it likewise forms strap slots for securing a plurality of straps thereto. Upper anterior and posterior strap slots 516, 517 are adapted to position a strap preferably about the exterior surface 503 of the unitary body 501 to better distribute circumferential pressure over the exterior surface 503 of the unitary body 501 and minimize such pressure directly on the user's leg. The sections of the exterior surface 503 over which straps secure to the unitary body 501 by the upper anterior and posterior strap slots 516, 517 may be polished (i.e., a polished surface 518) to reduce the friction of the strap against the exterior surface 503. The anterior slots (there being slots on both the first and second portions 502, 504 corresponding to one another) are generally arranged adjacent to and parallel to the anterior peripheries of the first and second portions 502, 504 to provide better leverage when closing or drawing the anterior peripheries of the first and second portions 502, 504 toward one another by tensioning of a strap extending through the slots. The exterior surface 503 may define recesses 520 to better position and retain the strap along the exterior surface 503.

The upper anterior and posterior strap slots 516, 517, and any other strap slots, just like with the polishing, may be slightly oversized relative to the width of the corresponding strap to prevent binding of the straps at the edges of the slots. Given the clamshell configuration of the orthopedic walker 500, the arrangement of the slots secure donning but enable easy opening of the "clamshell" configuration relationship of the first and second portions 502, 504 relative to one another.

Figure 22A:
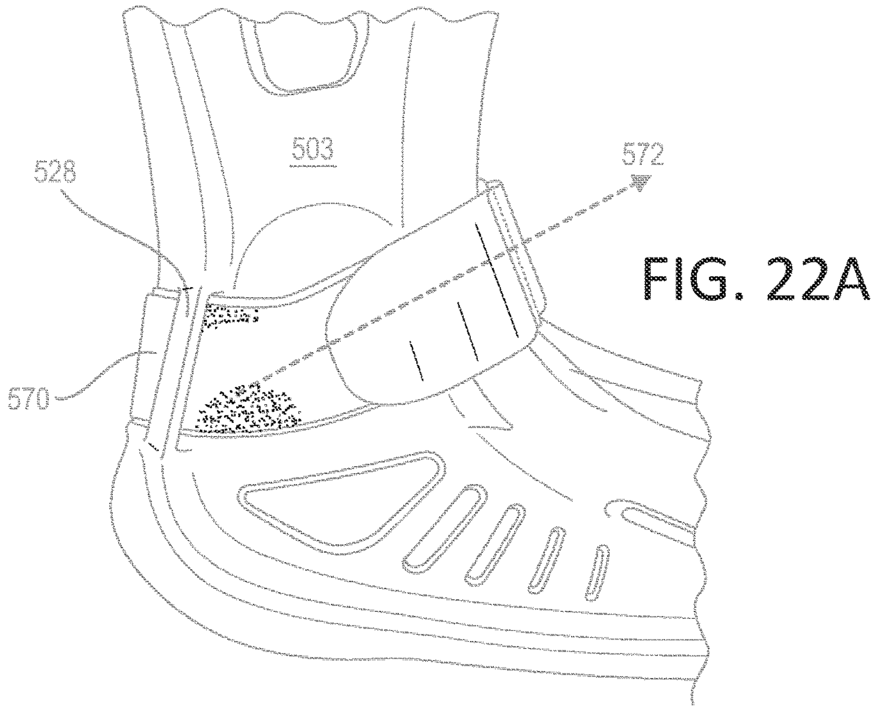
FIG. 22A is an exemplary view of an ankle strap on the orthopedic walker of FIG. 20A.
Figure 22B:
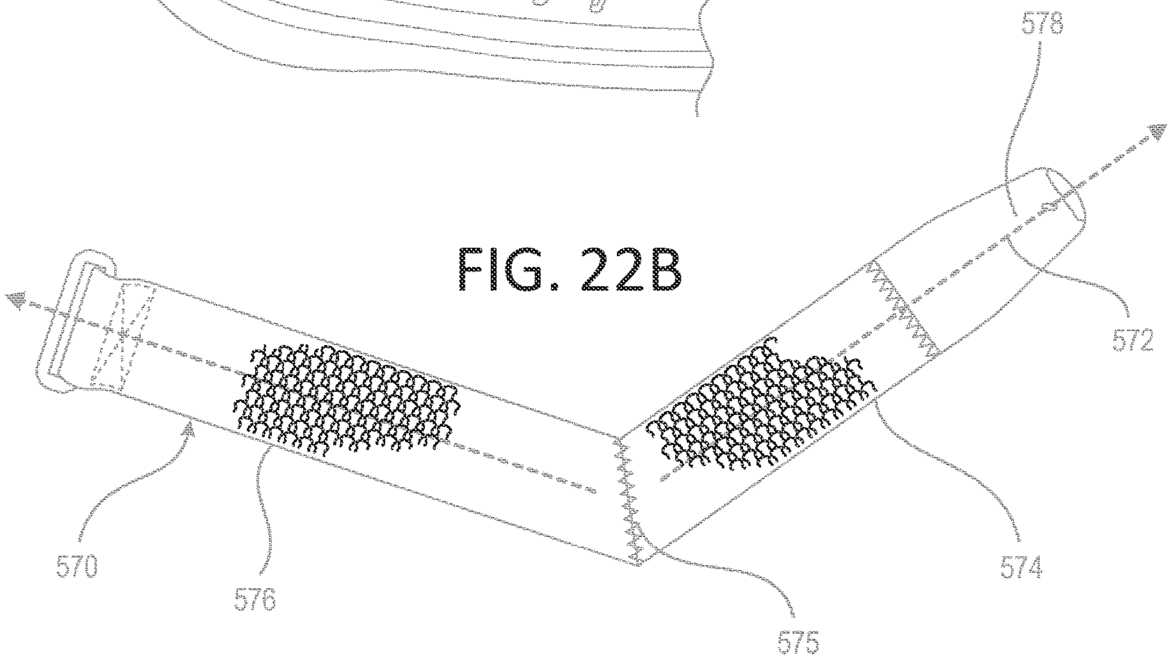
FIG. 22B is a plan view of the ankle strap of FIG. 22A.
Figure 22C:
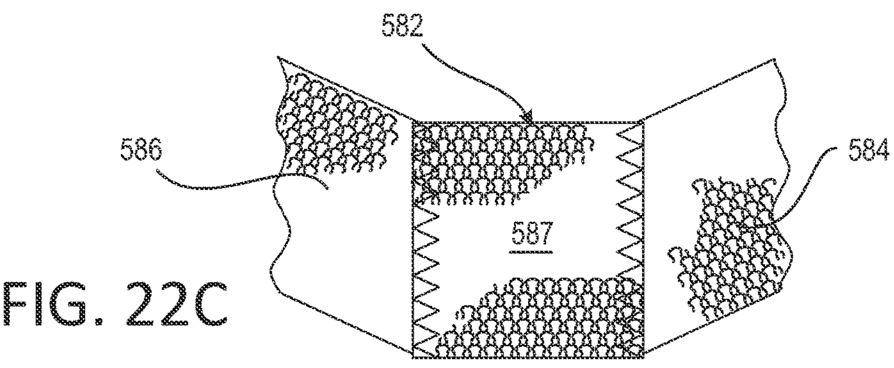
FIG. 22C is a sectional view of a variation of the ankle strap of FIG. 22A.

Similarly, the unitary body 501 forms slots 528 for an ankle strap, described in more detail in FIGS. 22A-22C, and recesses 530 for extending over the peripheries of the first and second portions 502, 504, thereby aligning the ankle strap appropriately over the exterior surface 503 of the unitary body 501. A toe strap may be connected to anterior/toe portion slots 534, described in more detail in FIGS. 25A, 25B. The angle by which the ankle strap is arranged is adapted to pull the user's heel into a corner of the orthopedic walker 500. The strap is on the body's exterior, and by not weaving the strap into the inside of the body, the orthopedic walker 500 enables more surface area for landing areas of hook and loop tabs.

A hook insert (not shown) may be inserted into a recess 532, and secured thereto. An exemplary hook insert is described in U.S. Pat. No. 9,474,334, granted Oct. 25, 2016, and incorporated herein by reference. The hook insert mitigates the need to use pressure-sensitive adhesive hook material, which tends to tear away from the orthopedic walker body over repeated uses.

The unitary body 501 defines added space or bulges 524, 526 generally corresponding to a user's malleolus, both at the interior and exterior of the unitary body 501. The bulges 524, 526 may protrude and create a recess of 5 to 15 mm, and more preferably 10 mm, relative to the adjacent interior and exterior surface 505, 503. The medial side of the unitary body 501 may have a greater bulge to accommodate a bony prominence the protrudes more than at the lateral side, thereby lateral and medial bulges may differ. However, since the orthopedic walker 500 is adapted for both right- and left legs, the bulges 524, 526 may create a concavity (interior surface) or convexity (exterior surface) that is the same on both first and second portions 502, 504. When the softgood assembly is inserted into the interior volume, it is arranged to fill any extra space created by the bulges if not take by the bony prominence at the malleolus of the user.

Figure 20A:
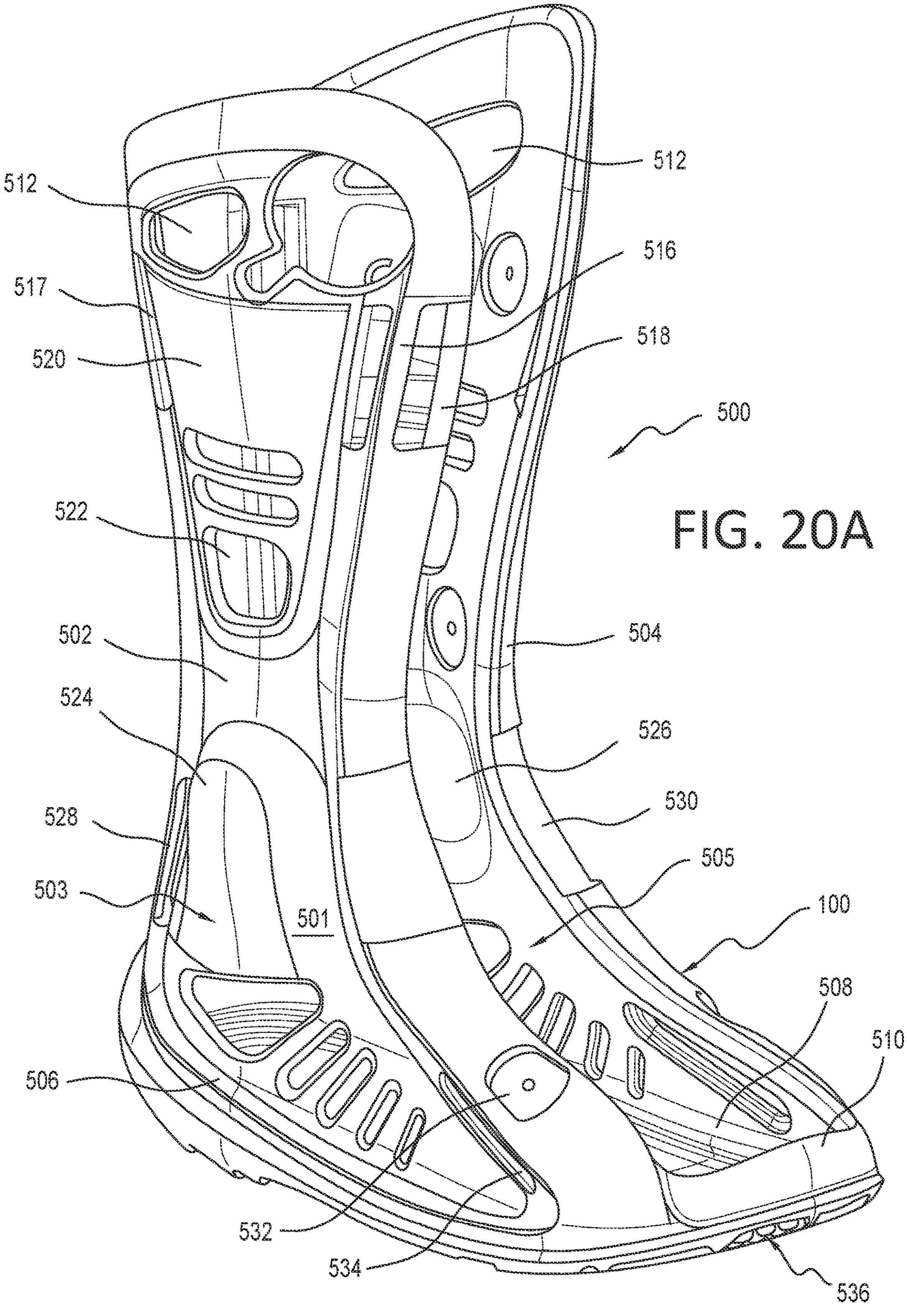
FIG. 20A is a perspective view of another embodiment of an orthopedic walker.
Figure 20B:
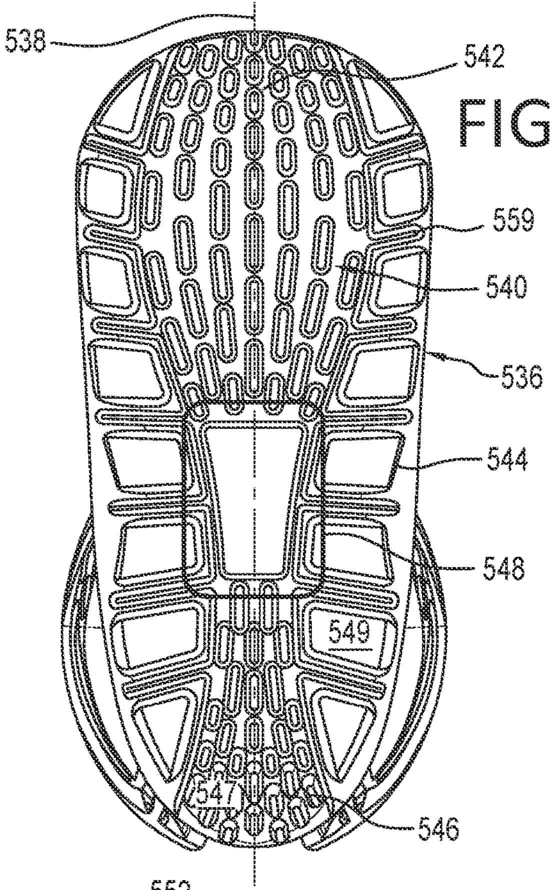
FIG. 20B is a bottom view of the orthopedic walker of FIG. 20A, showing the outsole.

FIG. 20B illustrates an outsole 536 to the orthopedic walker 500. The outsole 536 has a longitudinal axis, extending in anterior and posterior directions, dividing the orthopedic walker 500 in lateral and medial sides, although the orthopedic walker 500 is universal because it is useable for right and left feet. The outsole 536 has a tread pattern 540 extending relative to the longitudinal axis 538 to increase slip resistance. The inner portion 547 of the tread pattern has elongate bosses extending about the longitudinal axis 538 narrowing toward a mid-foot part 544. The toe and heel portions 542, 546 may curve upwardly, as illustrated in FIG. 20D. The outer portion 549 of the tread pattern defines wider bosses with channels 560 therebetween.

The outsole 536 may be sandblasted for additional grip. The tread pattern of the outsole 536, with the sandblasting, is adapted to promote liquid being squeezed outwardly from at least the channels 559 for enhanced slip-resistance on wet surfaces. The outsole defines a larger center boss 548, compared to the bosses of the inner and outer portions 547, 549, at a mid-foot or apex of the outsole 536. The center boss 548 is provided at a location to create a neutral balance point to maximize the surface area of the outsole when standing.

Figure 20C:
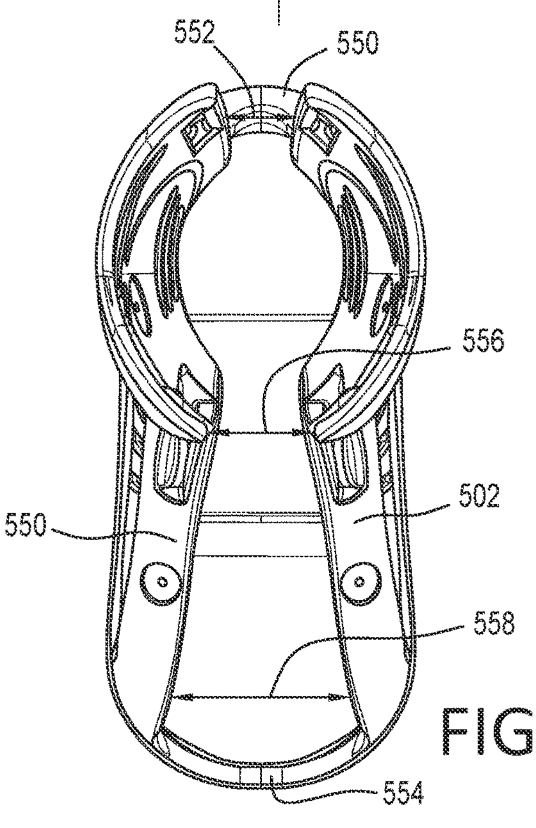
FIG. 20C is a top view of the orthopedic walker of FIG. 20A.
Figure 20D:
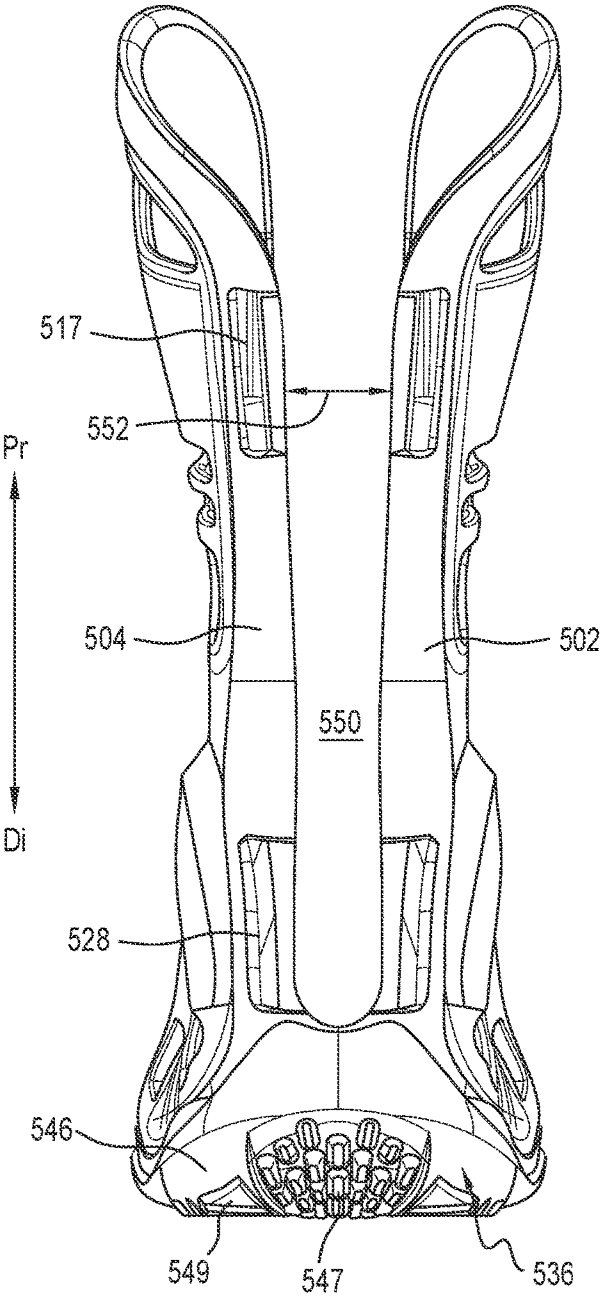
FIG. 20D is a rear view of the orthopedic walker of FIG. 20A.

FIGS. 20C and 20D exemplify clearances between the first and second portions 502, 504. The posterior clearance 550 is narrower than the anterior clearance 556, corresponding to the user's upper leg. The posterior clearance 550 may taper in the distal direction $D_i$ toward the footbed 506 of the unitary body 501 from the proximal direction $P_r$ of the orthopedic walker 500. The distance between the first and second portions 502, 504 is greater below the anterior clearance 556 and extending over the dorsal aspect of a user's foot at the dorsal or toe box clearance 558. The toe box clearance 558 is at its greatest at the anterior end 554 of the footbed 506 and continuously tapers posteriorly to the anterior clearance 556. This arrangement of the toe box clearance 558 makes it easier to don and doff the orthopedic walker without opening the posterior and anterior clearances 550, 556 at the lower leg as much.

It has been found that to avoid improper expansion of the posterior clearance 550, a critical clearance or width 552 of the posterior clearance 550 is established, generally a mid-height of the upper posterior strap slots 517. Depending on the rigidity of the polymeric material forming the orthopedic walker, it may be desirable to provide means for maintaining the critical clearance or width 552 from expanding. For example, the critical clearance may be 30-40 mm, or more preferably 35 mm.

FIGS. 21A-21D illustrate different means the critical clearance can be maintained, at least from expanding. FIG.

Figure 21A:
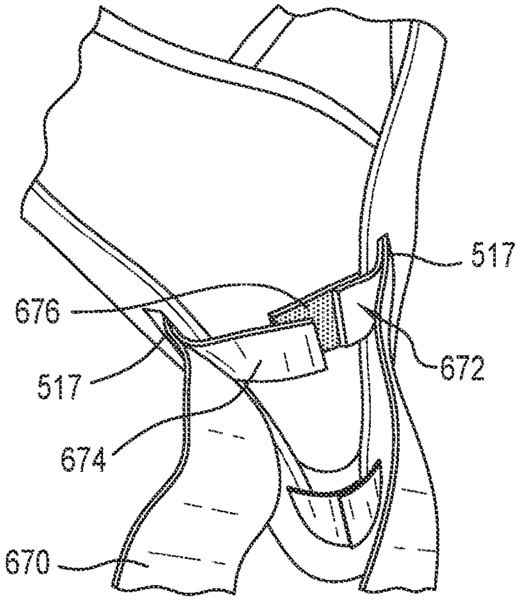
FIG. 21A is an embodiment of a strap block in the orthopedic walker of FIG. 20A.
Figure 21B:
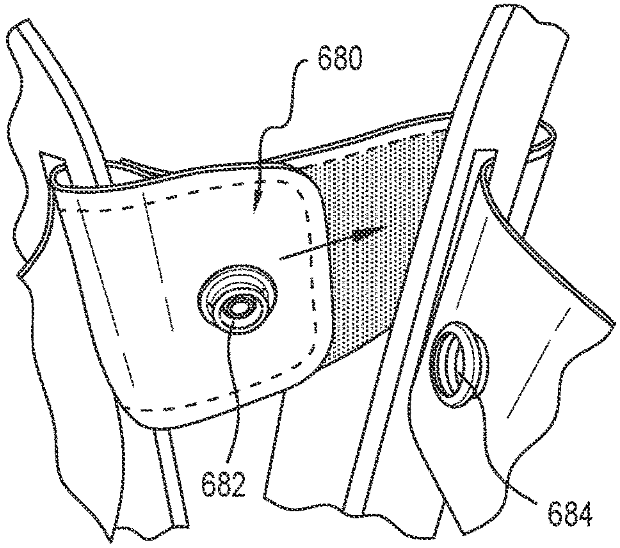
FIG. 21B is another embodiment of a strap block in the orthopedic walker of FIG. 21A.

21A shows a substrap 672 secured between the upper posterior strap slots 517 of the unitary body 501. The substrap 672 has a landing 676 that defines the critical clearance and a tab 674 adapted to secure the landing 676, preventing the expansion of the critical distance. A posterior strap 670 may extend over the substrap 672 without interference. FIG. 21B shows a substrap 680 having first and second fasteners 682, 684 spaced from one another to define the critical clearance.

Figure 21C:
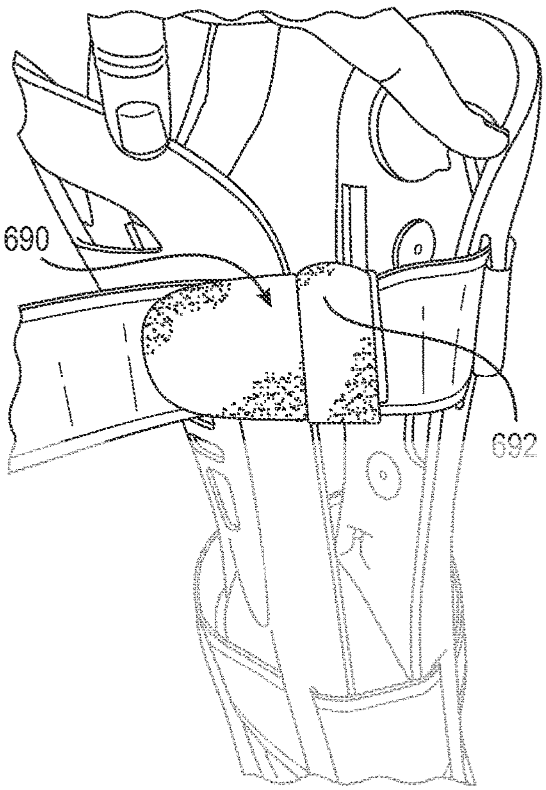
FIG. 21C is another embodiment of a strap block in the orthopedic walker of FIG. 21A.
Figure 21D:
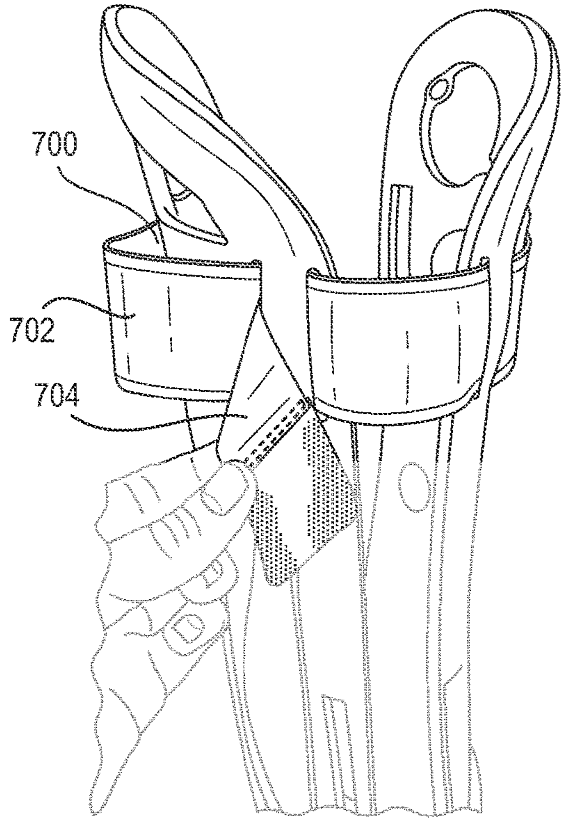
FIG. 21D is another embodiment of a strap block in the orthopedic walker of FIG. 21A.

FIG. 21C defines a strap blocker 692 on a substrap 690 that prevents the substrap 690 from expanding a width between the first and second portions 502, 504 beyond the critical clearance. FIG. 21D defines a posterior strap 700 having a main body 702, and a substrap 704 underlies the main body 702. The substrap 704 is secured to the main body 702 and can individually extend between the first and second portions 502, 504, to the critical clearance.

By providing an orthopedic walker according to embodiments of the disclosure, an orthopedic walker may combine the benefits of existing casting devices and existing orthopedic braces in a walker that is both lightweight compared to existing devices and nevertheless comprises necessary strength and rigidity for immobilization and support of a limb of a user.

FIGS. 22A-22C illustrate an ankle strap 570 useable in the orthopedic walker 500. As shown in FIG. 22A, the ankle strap 570 is oriented from the posterior slot 528 obliquely in a proximal direction 572 away from the foot bed. The oblique direction promotes better fitment and draws the user's heel and ankle into posterior distal corner of the orthopedic walker.

FIG. 22B depicts how the ankle strap 570 is oriented in angled segments 574, 576 extending from a posterior junction 575. Each angled segment 574, 576 extends in an oblique angle (relative to the posterior junction generally aligned to a vertical axis). The angle defined between the angled segments may be 110 to 130 degrees, preferably at 120 degrees. The angled segments 574, 576 are arranged to secure to one another. One angled segment has a fastener tab 578 and the other angled segment having a loop through which the fastener tab 578 extends and loops about to secure over a surface of the ankle strap 570 via hook-and-loop fasteners. The material of the angled segments may include loop material adapted to engage fastening material of the fastener tab 578.

FIG. 22C illustrates a variation of the junction 582 that includes a posterior segment 587 from which the angled segments 584, 586 extend. The posterior segment 587 is adapted to distribute pressure evenly over the posterior of the body 501 of the orthopedic walker. As with the strap embodiments, the surface of the ankle strap 570 may have a loop surface 587, adapted to engage with and secure to hook elements of the fastener tab 578.

FIGS. 23A-23C depict mounting of a pump 610 to the unitary body 501 at an opening 600 fitted for receiving the pump 610. The opening 600 includes a narrowing or crimp portion 602 adapted to fit to a transition portion 616 of the pump 610 leading to a stem 617 and valve 618. A mounting portion 614 of the pump 610 can extend into a first aperture 606 defined by a thickness of the unitary body 501 at one end, and a second aperture 620 for receiving the pin 619 of the pump 610.

The unitary body 501 defines a wall 608 having a variable thickness 609 adapted to form the first aperture 606 as needed, and the variable thickness 609 and wall 608 about the opening 600 is arranged to snugly secure to the pump 610, thereby enabling a bulbous portion 612 of the pump 600 to function without interference by the unitary body 501. The pump 610 can advantageously be removed from the unitary body 501, along with a softgood assembly, as needed by a clinician to fit the orthopedic walker 500 or by a user. The valve 618 can protrude from the unitary body's 501 exterior for easy access for regulating the air pressure in a bladder belonging to the softgood assembly.

FIGS. 24A-24C illustrate a softgood support assembly 630. The softgood support assembly 630 includes a softgood boot 632 approximating the interior volume of the body of the orthopedic walker. A bladder 634 is disposed on the exterior of the softgood boot 632 and is adapted to connect to the pump 610 of FIGS. 23A-23C by an inflation tube 650. The bladder 634 is preferably secured by a tab 648 to the softgood boot 632, and the tab 648 enables displacement of the bladder 634 relative to the softgood boot 632 when inflated, as a distal portion of the bladder 634 may be secured to the edges of a sole portion 642 of the softgood, thereby cantilevering, if necessary relative to the sole portion 642 when inflated. The bladder 634, when inflated, can fill voids and crevices in the inner volume of the unitary body 501, including the malleolus mentioned above bulges to offer a secure fit of the orthopedic walker to the user's foot and lower leg.

FIG. 24B depicts the softgood boot 632 as having first and second portions 636, 638 that are intended to wrap about the lower leg, and secure to one another by a fastener 646 (such as hook and loop material). The first and second portions 636, 638 may be connected by a posterior seam so they can articulate about the lower leg relative to one another. A heel portion 640 connects the first and second portions 636, 638 to the sole portion 642.

As shown in FIG. 23C, the bladder 634 may have a unitary construction whereby the pump 610 inflates the entire bladder 634. While the bladder 634 may have first and second (lateral or medial) portions 652, 654, they are fluidly connected to one another by a posterior portion 656 that may wrap about a user's heal in the softgood boot 632.

Figure 25A:
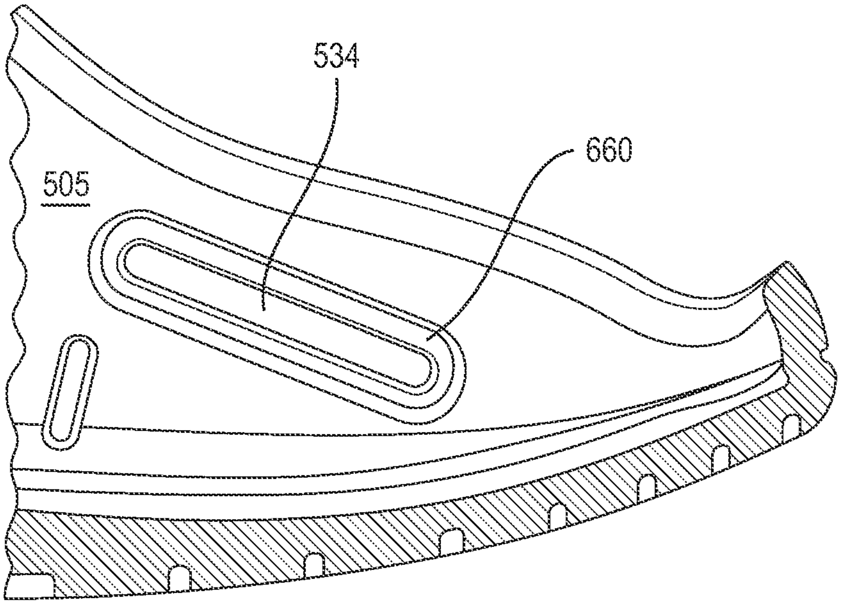
FIG. 25A is a sectional view of an interior surface of the orthopedic walker of FIG. 20A at a toe region.
Figure 25B:
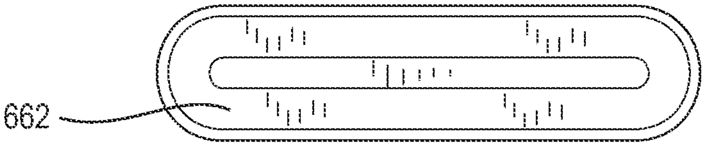
FIG. 25B is a plan view of a stopper for insertion in a recess of the toe region in FIG. 25A.

FIGS. 25A and 25B illustrate how due to the molded construction of the unitary body 501, the interior (or exterior) may be provided with features to mitigate use of hook and loop material. In this example, the interior surface 505 defines a recess 660 about the toe portion slot 534 for a toe strap (not shown). The toe strap may have one end secured to a stopper 662 form-fitted to the recess 660 to be flush with the interior surface 505.

Figure 26:
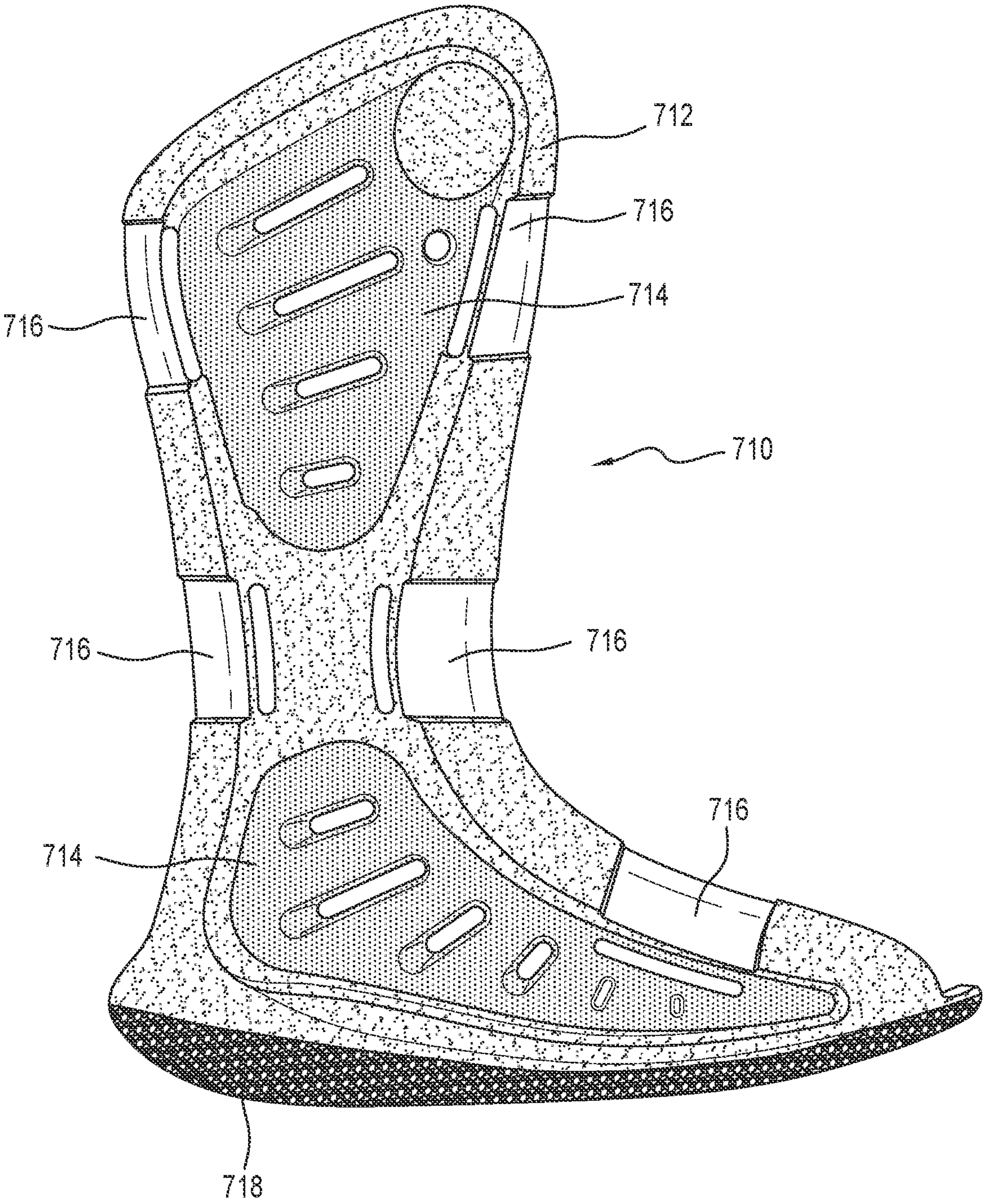
FIG. 26 is an elevational view of the exemplifying the orthopedic walker of FIG. 1 having different surface textures.

FIG. 26 demonstrates an orthopedic walker 710 similar to the orthopedic walker 100 of FIG. 1 having various "functional" surface textures along an exterior surface 103 of the orthopedic walker 100. A significant advantage to an orthopedic walker formed from an expanded polymeric material and in which the expanded polymeric material forms the entire body of the orthopedic walker inclusive of the sole or tread, is that areas of the orthopedic walker can be adapted with such functional surface textures. Unlike dual strut orthopedic walkers, or circumferential walkers formed from different material compositions, the expanded polymeric material can be molded to have functional characteristics.

FIG. 26 exemplifies that the main body of the orthopedic walker 710 can have a smooth or conventional surface texture 712. Such surface texture is neither particularly rough, as in the sole area 718, which is used for comparatively greater traction control against a walking surface, or particularly smooth as in polished areas 716 along which straps slide. Likewise, other contrasting areas of the orthopedic walker 710 may have a surface texture different from the surface texture 712 for aesthetic purposes.

Surface textures may comply to the Mold Tech Texture standards also Mold-Tech texture specifications. Area 712 may have a mold tech series number MT-11050 or equivalent with a texture depth (m) of 0.1143 and a draft angle of 6.5. Area 714 may have a mold tech series number MT-11010 with a texture depth (m) of 0.0254 and a draft angle of 1.5. The polished areas 716 may have a mold tech series number MT-11030 with a texture depth (m) 0.0508 with a draft angle of 3. The sole area 718 may have any type of significantly greater textures surface texture over the aforementioned surface textures.

Additionally, another advantage to molding the body with different surface textures is that logos, sizes and other indicia may be molded into the body at predetermined locations. Likewise, such logos, sizes and other indicia can be provided with their own surface textures to offer contrasting and/or identifiable characteristics, as desired. Thus, the ability to mold an entire body from an expanded polymeric material is advantageous over known orthopedic walkers formed from perhaps more rigid materials and/or a plurality of assembled components.

According to the embodiments, orthopedic walkers may comprise additional features for supporting a limb of a user without adding significant weight, such as stays or inserts, ventilation openings, longitudinal openings facilitating supine donning and doffing removable outer soles, and others.

It is to be understood that not necessarily all objects or advantages may be achieved under an embodiment of the disclosure. Those skilled in the art will recognize that an orthopedic walker may be embodied or carried out so it achieves or optimizes one advantage or group of advantages as taught herein without achieving other objects or advantages as taught or suggested herein.

The skilled artisan will recognize the interchangeability of various disclosed features. Besides the variations described, other known equivalents for each feature can be mixed and matched by one of ordinary skill in this art to build and use an orthopedic device under principles of the present disclosure. The skilled artisan will understand that the features described may be adapted to other methods and types of orthopedic and prosthetic devices.

Although this disclosure describes certain exemplary embodiments and examples of an orthopedic walker, it will be understood by those skilled in the art that the present disclosure extends beyond the specifically disclosed patellofemoral support to other alternative embodiments and/or uses of the disclosure and obvious modifications and equivalents thereof, including other types and components of orthopedic, prosthetic, and medical devices. It is intended that the present disclosure should not be limited by the disclosed embodiments described above and may be extended to other applications that may employ the features described.

The invention claimed is:

1. An orthopedic walker comprising:

a body formed from at least one polymeric material and having a unitary construction;

the body forming first and second portions divided by a median plane and connected to one another by a footbed, the first and second portions extending from the footbed and forming an interior volume for receiving a foot and lower leg of a user;

the body consisting of the first and second portions and the footbed, wherein the footbed is inclusive of an outsole having a tread as a continuous structure formed unitarily from the at least one polymeric material, the at least one polymeric material being an expanded thermoplastic selected from the group consisting of polyurethane, polyethylene, polypropylene and ethylene-vinyl acetate;

the body forming an anterior opening extending from a toe region to a proximal edge of the body, the anterior opening defining a clearance between first and second edges of the first and second portion, the clearance having a variable width as it extends distally from the proximal edge;

the body forming a posterior opening extending from the proximal edge of the body to the footbed, the posterior opening tapering in width as it extends distally to a terminus;

wherein the first and second portions are arranged to articulate about or from the median plane to expand and retract the interior volume;

wherein the body forms a rough functional surface texture on the outsole and at least one smooth functional surface texture on the first and second portions, the rough functional surface texture having a greater texture depth than the smooth functional surface texture;

wherein a calf aspect of the body is placed more posteriorly according to a relative extension from a footbed aspect;

wherein the calf aspect intersects an apex of an outsole contour, such that a rocker configuration of the outsole contour is neutral at standing;

wherein an insole contour defines a toe raise, the toe raise being greater than a heel height;

wherein the tread of the outsole is formed unitarily and integrated with the body of the walker thereby negating a need of adhesion of a separate outsole tread to the walker;

wherein the tread comprises:

an inner portion having elongate bosses extending about the median plane and narrowing toward a mid-foot part;

an outer portion having wide bosses separated by channels formed on the tread, the wide bosses being wider than the elongate bosses; and a central boss defining a neutral balance point along the outsole contour, wherein the central boss has a greater surface area than each of the elongate bosses and the wide bosses.

2. The orthopedic walker of claim 1, wherein the first and second portions have a same profile such that the interior volume is arranged for both right and left legs of the user, and the footbed arranged for both right and left feet of the user.

3. The orthopedic walker of claim 1, further comprising at least one strap extending over at least part of an exterior surface of the body and along an interior surface of the body, and across at least one of the anterior and posterior openings.

4. The orthopedic walker of claim 3, wherein the at least one strap is secured to the body without adhesives.

5. The orthopedic walker of claim 4, wherein the at least one strap is arranged to extend along the interior surface and the exterior surface of the body while spanning the anterior and posterior openings, thereby forming a circumferential strap system about the orthopedic walker.

6. The orthopedic walker of claim 1, further comprising a pump secured to the body, the pump fitting in an opening formed by the first portion of the body, a valve communicating with the pump and fitting in another opening formed by the first portion, the pump and the valve extending from an exterior surface of the first portion and communicating with a liner inserted in the interior volume and having a bladder for inflation and regulation by the pump and the valve.

7. The orthopedic walker of claim 1, wherein the first portion defines at least a first region about at least an exterior surface of the body, the first region being demarcated from a connecting region adjacent the first region, the first region having a different color or surface texture from the connecting region.

8. The orthopedic walker of claim 7, wherein the body forms at least one ventilation opening including at least two ventilation openings arranged in shape corresponding to a shape of the first region.

9. The orthopedic walker of claim 1, wherein the footbed defines a heel roll region at a posterior end of the footbed, the heel roll region having a heel extension protruding posteriorly of the first and second portions and extending the outsole and heel roll region.

10. The orthopedic walker of claim 9, wherein the footbed defines a maximum stack height of a heel lift relative to the toe region, with the insole increasing in height relative to the outsole posteriorly.

11. The orthopedic walker of claim 9, wherein the heel extension extends a predetermined distance posteriorly from a terminus of the first and second portions at a junction of the footbed.

12. The orthopedic walker of claim 1, wherein the first portion defines an anterior arch extending over the footbed, the anterior arch having a thickness along the first edge tapering in a first thickness aspect distally toward the footbed.

13. The orthopedic walker of claim 12, wherein the thickness of the anterior arch being greatest along the first edge, the anterior arch having increased material anteriorly for immobilization of an ankle;

wherein the anterior arch has greater thickness than adjacent areas, the anterior arch forming a generally arcuate portion of the body along an anterior side, the anterior arch providing reinforcement for sagittal plane immobilization.

14. The orthopedic walker of claim 1, further comprising a sole insert for placement within the footbed and along an interior surface of the insole;

wherein the insole defines at least one channel disposed along a midline of the footbed, the at least one channel facilitating articulation of the first portion relative to the second portion in first and second directions for enlarging the anterior and posterior openings.

15. An orthopedic walker comprising:

a body formed from at least one polymeric material and having a unitary construction;

the body forming first and second portions divided by a median plane and connected to one another by a footbed, the first and second portions extending from the footbed and forming an interior volume for receiving a foot and lower leg of a user;

the body consisting of the first and second portions and the footbed, wherein the footbed is inclusive of an outsole having a tread as a continuous structure formed unitarily from the at least one polymeric material, the at least one polymeric material being an expanded thermoplastic consisting ethylene-vinyl acetate;

the body forming at least one strap slot, a portion of the body about and proximate the at least one strap slot has a polished surface texture different from an area adjacent the polished surface texture;

the body forming an anterior opening extending from a toe region to a proximal edge of the body, the anterior opening defining a clearance between first and second edges of the first and second portion, the clearance having a variable width as it extends distally from the proximal edge;

the body forming a posterior opening extending from the proximal edge of the body to the footbed, the posterior opening tapering in width as it extends distally to a terminus;

at least one strap extending over at least part of an exterior surface and along an interior surface, and across at least one of the anterior and posterior openings, the at least one strap arranged to extend along the interior surface and the exterior surface of the body while spanning the anterior and posterior openings, thereby forming a circumferential strap system about the orthopedic walker;

wherein the body forms a rough functional surface texture on the outsole and at least one smooth functional surface texture on the first and second portions, the rough functional surface texture having a greater texture depth than the smooth functional surface texture;

wherein a calf aspect of the body is placed more posteriorly according to a relative extension from a footbed aspect;

wherein the calf aspect intersects an apex of an outsole contour, the outsole contour having a neutral balance point at the apex such that a rocker configuration of the outsole contour is neutral at standing;

wherein an insole contour defines a toe raise, the toe raise being greater than a heel height;

wherein the tread of the outsole is formed unitarily and integrated with the body of the walker thereby negating a need of adhesion of a separate outsole tread to the walker;

wherein the tread comprises:

an inner portion having elongate bosses extending about the median plane and narrowing toward a mid-foot part;

an outer portion having wide bosses separated by channels formed on the tread, the wide bosses being wider than the elongate bosses; and a central boss forming the neutral balance point along the outsole contour, wherein the central boss has a greater surface area than each of the elongate bosses.

16. The orthopedic walker of claim 15, wherein the first and second portions are arranged to articulate about or from the median plane to expand and retract the interior volume.

17. An orthopedic walker comprising:

a body formed from at least one polymeric material and having a unitary construction;

the body forming first and second portions divided by a median plane and connected to one another by a footbed, the first and second portions extending from the footbed and forming an interior volume for receiving a foot and lower leg of a user;

the body consists of the first and second portions and the footbed inclusive of an outsole having a tread as a continuous structure formed unitarily from the at least one polymeric material, the at least one polymeric material being an expanded thermoplastic consisting ethylene-vinyl acetate;

a pump secured to the body, the pump fitting in an opening formed by the first portion of the body, a valve communicating with the pump and fitting in another opening formed by the first portion, the pump and the valve extending from an exterior surface of the first portion;

a liner communicating with the valve and pump, the liner arranged to be inserted in the interior volume and having a bladder for inflation and regulation by the pump and the valve;

wherein the body forms a rough functional surface texture on the outsole and at least one smooth functional surface texture on the first and second portions, the rough functional surface texture having a greater texture depth than the smooth functional surface texture;

wherein a calf aspect of the body is placed more posteriorly according to a relative extension from a footbed aspect;

wherein the calf aspect intersects an apex of an outsole contour, such that a rocker configuration of the outsole contour is neutral at standing;

wherein an insole contour defines a toe raise, the toe raise being greater than a heel height;

wherein the tread of the outsole is formed unitarily and integrated with the body of the walker thereby negating a need of adhesion of a separate outsole tread to the walker;

wherein the tread comprises:

an inner portion having elongate bosses extending about the median plane and narrowing toward a mid-foot part;

an outer portion having wide bosses separated by channels formed on the tread, the wide bosses being wider than the elongate bosses; and a central boss defining a neutral balance point along the outsole contour, wherein the central boss has a greater surface area than each of the wide bosses.

18. The orthopedic walker of claim 1, further comprising a heel wedge adapted to fit within the interior volume contour to the insole and an interior surface of the body, wherein the heel wedge includes at least two layers having interlocking features arranged to lock the at least two layers relative to one another.

* * * * *